US010286061B2

(12) United States Patent
Tobin et al.

(10) Patent No.: US 10,286,061 B2
(45) Date of Patent: May 14, 2019

(54) IMMUNOGENIC INFLUENZA COMPOSITION

(71) Applicant: Biological Mimetics Inc., Frederick, MD (US)

(72) Inventors: Gregory J Tobin, Frederick, MD (US); Peter L Nara, Frederick, MD (US); George Lin, Bloomsburg, PA (US)

(73) Assignee: Biological Mimetics, Inc., Frederick, MD (US)

( * ) Notice: Subject to any disclaimer, the term of this patent is extended or adjusted under 35 U.S.C. 154(b) by 0 days.

(21) Appl. No.: 14/793,732

(22) Filed: Jul. 7, 2015

(65) Prior Publication Data

US 2018/0071383 A1 Mar. 15, 2018

Related U.S. Application Data

(63) Continuation of application No. 13/574,779, filed as application No. PCT/US2011/022280 on Jan. 24, 2011, now abandoned.

(60) Provisional application No. 61/297,762, filed on Jan. 24, 2010.

(51) Int. Cl.

| | |
|---|---|
| ***A61K 39/145*** | (2006.01) |
| ***C07K 16/10*** | (2006.01) |
| ***A61K 39/12*** | (2006.01) |
| *A61K 39/00* | (2006.01) |

(52) U.S. Cl.

CPC ............ *A61K 39/145* (2013.01); *A61K 39/12* (2013.01); *C07K 16/1018* (2013.01); *A61K 2039/5258* (2013.01); *A61K 2039/545* (2013.01); *A61K 2039/55566* (2013.01); *A61K 2039/70* (2013.01); *C07K 2317/33* (2013.01); *C07K 2317/76* (2013.01); *C12N 2760/16034* (2013.01); *C12N 2760/16134* (2013.01)

(58) Field of Classification Search

None

See application file for complete search history.

(56) References Cited

U.S. PATENT DOCUMENTS

| | | | | |
|---|---|---|---|---|
| 5,041,376 A * | 8/1991 | Gething | C07K 14/005 | 435/466 |
| 5,853,724 A | 12/1998 | Garrity | | |
| 7,090,973 B1 * | 8/2006 | Breton | C07K 14/195 | 435/6.19 |
| 9,872,899 B2 | 1/2018 | Tobin et al. | | |
| 2006/0051747 A1 * | 3/2006 | Pau | A61K 39/145 | 435/5 |
| 2015/0313989 A1 * | 11/2015 | Nara | A61K 39/12 | 424/209.1 |

OTHER PUBLICATIONS

Baker et al., Protein Structure Predication and Structural Genomics, Science (2001) vol. 294, No. 5540, pp. 93-96 (Year: 2001).*

Attwood, T. The Babel of Bioinformatics, Science (2000) vol. 290, No. 5491, pp. 471-473 (Year: 2000).*

Zhu et al. Abstract Only. A naturally occurring deletion in its NS gene contributes to the attenuation of an H5N1 swine influenza virus in chickens. J Virol. Jan. 2008;82(1):220-8. (Year: 2008).*

Padlan. Designing Vaccines against Constantly Mutating Pathogens. 2006. Manilla Bulletin-online article. (Year: 2006).*

Martinet et al. Evaluation of recombinant A/Victoria/3/75 (H3N2) influenza neuraminidase mutants as potential broad-spectrum subunit vaccines against influenza A. Arch Virol. 1998;143(10):Sep. 2011. (Year: 1998).*

Schoofs et al. Epitopes of an influenza viral peptide recognized by antibody at single amino acid resolution. J Immunol. Jan. 15, 1988;140(2):611-6. (Year: 1988).*

Quan et al. Virus-like particle vaccine induces protective immunity against homologous and heterologous strains of influenza virus. J Virol. Apr. 2007;81(7):3514-24. (Year: 2007).*

GenBank: EEV87622 (2013) (Year: 2013).*

* cited by examiner

*Primary Examiner* — Michelle S Horning

(74) *Attorney, Agent, or Firm* — MDIP LLC

(57) ABSTRACT

Methods for providing novel compositions useful as influenza immunogens are provided. The compositions enable a host response to immunogen sites normally not recognized by a host. The novel immunogens can be used as vaccines or to develop antibodies.

13 Claims, 5 Drawing Sheets

Specification includes a Sequence Listing.

Table 1. Results of testing immune refocused HA antigens

| Hemagglutination Inhibition Titers* Test Viruses (increasing variation -->) | | | | | Virus Neutralization Titers Test Viruses (increasing variation -->) | | | | |
|---|---|---|---|---|---|---|---|---|---|
| HA Antigen | Cal/04/ 2009 | Strain 2 | Strain 3 | Strain 4 | HA Antigen | Cal/04/ 2009 | Strain 2 | Strain 3 | Strain 4 |
| Mock (neg) | ND** | ND | ND | ND | Mock (neg) | ND | ND | ND | ND |
| WT-HA | 512 | 128 | 64 | ND | WT-HA | 256 | 64 | 32 | ND |
| Mut-H1 | 512 | 512 | 256 | 256 | Mut-H1 | 256 | 256 | 128 | 128 |
| Mut-H2 | 512 | 256 | 256 | 128 | Mut-H2 | 256 | 128 | 128 | 64 |
| Mut-H3 | 512 | 256 | 256 | 64 | Mut-H3 | 256 | 128 | 128 | 32 |

* Titers are expressed as reciprocal serum dilutions

** ND signifies "not detectable in this assay"

Figure 1

Table 2 Single-Site Immune Refocusing HA mutants of California/04/2009

| Mutation | Site | Sequences |
|---|---|---|
| WT | | 33 LEDKHNGKLCKLRGVAPLH |
| M1 | C | 33 -NST--------------- |
| M2 | C | 33 --------NVT-------- |
| M3 | C | 33 -QNI--------------- |
| M4 | C | 33 ----------I-L----- |
| WT | | 65 NPECESLSTASSWS |
| M5 | E | 65 ---------NIT-- |
| M6 | E | 65 NST----------- |
| M7 | E | 65 --Q-Q--------- |
| WT | | 118 PKTSSWPNHDSNKGVTAACPHAGAKS |
| M8 | A | 118 -NAS---------------------- |
| M9 | A | 118 ---------NIT-------------- |
| M10 | A | 118 ---------------------NATQ- |
| M11 | A | 118 -I------------------------ |
| M12 | A | 118 ---------N--I------------- |
| M13 | A | 118 --------------------N---L- |
| WT | | 153 KKGNSYPKLSKSYINDKGKEV |
| M14 | B | 153 -NAT----------------- |
| M15 | B | 153 IL------------------- |
| M16 | B | 153 -NAT-T--------------- |
| M17 | B | 153 -I----N-------------- |
| M18 | D | 153 ---------------VNGTQ- |
| M19 | D | 153 ----------------L-IQ- |
| WT | | 193 QNADTY 214 IAIRPKVRDQ |
| M20 | B | 193 ---S-- |
| M21 | B | 193 IA--- |
| M22 | D | 214 -----NVT-- |
| WT | | 233 LVEPGDKITFE 314 LATGLRNIPS |
| M23 | D | 233 ----NAT---- |
| M24 | D | 233 -----NL---- |
| M25 | f | 314 -----NIT-- |
| M26 | f | 314 -----I---- |

Figure 2

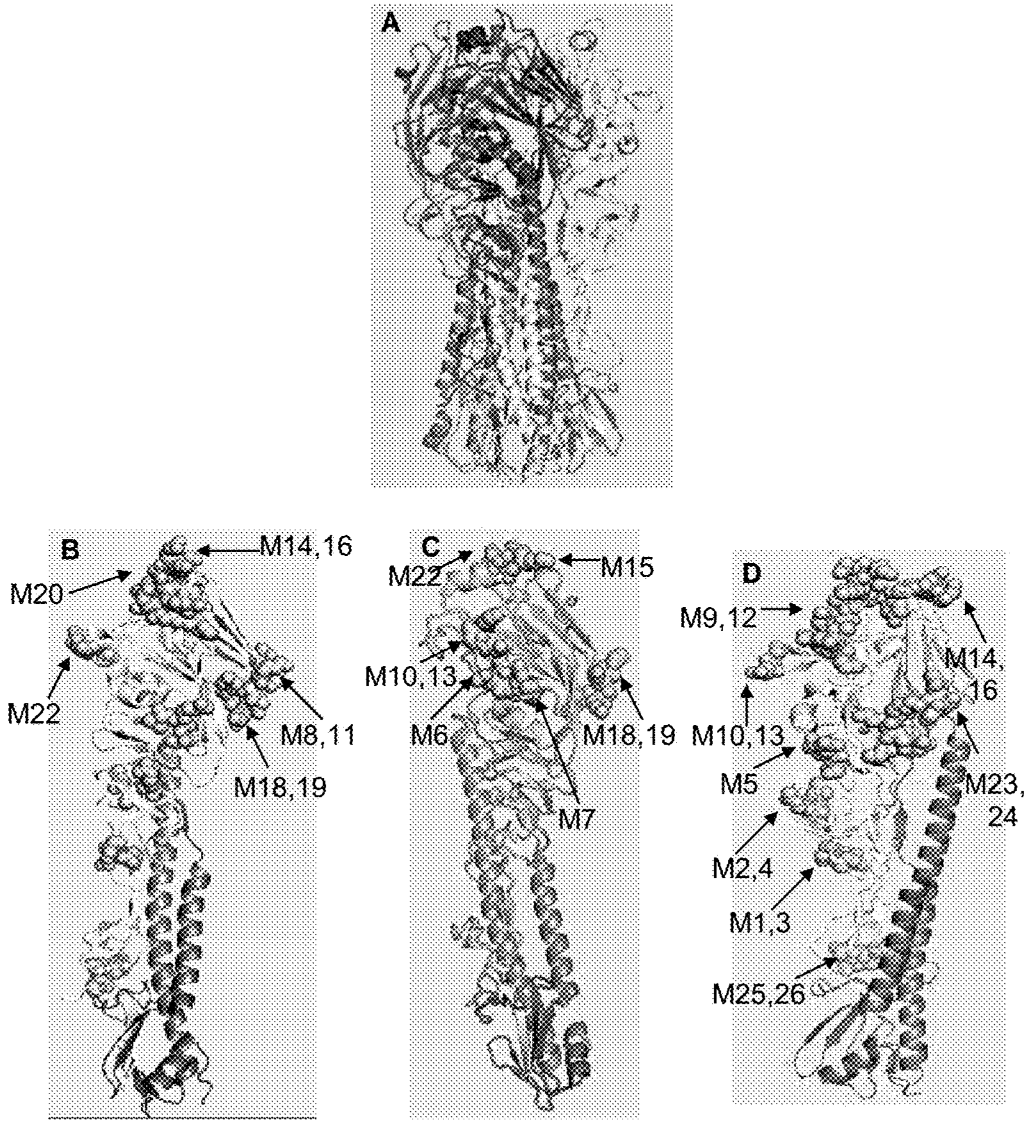
Figures 3A-3D. Approximate location of immune refocusing example mutations on a representative H1N1 HA molecule.

Table 3 Example of Mutations Composed of Combinations of two or three single-site mutations

| Mutation | Components | Epitopes |
|---|---|---|
| M27 | M1+M5 | C + E |
| M28 | M1+M6 | C + E |
| M29 | M3+M5 | C + E |
| M30 | M3+M7 | C + E |
| M31 | M8+M15 | A + B |
| M32 | M9+M14 | A + B |
| M33 | M8+M20 | A + B |
| M34 | M12+M15 | A + B |
| M35 | M1+M5+M9 | C + E + A |
| M36 | M1+M5+M12 | C + E + A |
| M37 | M1+M5+M14 | C + E + B |
| M38 | M3+M7+M15 | C + E + B |
| M39 | M3+M7+M20 | C + E + B |
| M40 | M1+M5+M14 | C + E + D |

Figure 4

Table 4. Combination mutations in all five epitopes

| Mutation | Components | Epitopes |
|---|---|---|
| M41 | M8 M20 M1 M22 M6 | ABCDE |
| M42 | M8 M20 M2 M22 M6 | ABCDE |
| M43 | M9 M14 M1 M22 M6 | ABCDE |
| M44 | M9 M14 M2 M22 M6 | ABCDE |
| M45 | M9 M20 M1 M22 M6 | ABCDE |
| M46 | M9 M20 M2 M22 M6 | ABCDE |
| M47 | M12 M15 M3 M14 M7 | ABCDE |
| M48 | M13 M15 M4 M14 M7 | ABCDE |
| M49 | M12 M17 M3 M14 M7 | ABCDE |
| M50 | M13 M17 M4 M14 M7 | ABCDE |

Figure 5

IMMUNOGENIC INFLUENZA COMPOSITION

BACKGROUND

The current stable of licensed vaccines in the human and veterinary arenas is generally successful against what are termed, "Class One pathogens." Class One pathogens (such as measles, mumps and rubella viruses) are those pathogens, which, in general: (1) infect or cause the most serious disease in infant, very young children, children and young adults; (2) carry a relatively stable microbial genome; (3) have a natural history of disease which results in spontaneous recovery; and (4) induce durable memory, associated with polyclonal and multi-epitope antigen recognition.

In contrast, Class Two pathogens, such as, influenza virus, HIV-1, malaria parasites, *Mycoplasma*, such as those that cause tuberculosis, Trypanosomes, Schistosomes, *Leishmania, Anaplasma*, Enteroviruses, Astroviruses, Rhinoviruses, Norwalk viruses, toxigenic/pathogenic *E. coli, Neisseria, Streptomyces*, nontypeable *Haemophilus* influenza viruses, Hepatitis C virus, cancer cells etc. are characterized by quite opposite features. For example, Class Two pathogens: (1) tend to infect and are transmitted in a significantly extended host age range, with infections occurring and reoccurring from childhood through the geriatric period; (2) exhibit microbial genetic instability in defined regions of their genome (a hallmark of the successful evolution of such pathogens); (3) in some cases, include spontaneous recovery of disease that frequently still leaves the host vulnerable to multiple repeated annual infections and/or the establishment of either a chronic/active or chronic/latent infectious state; (4) induce oligoclonal, early immune responses that are directed to a very limited set of immunodominant epitopes which provide either narrow strain-specific protection, no protection and/or enhanced infection; and (5) cause immune dysregulation following infection or vaccination, e.g. epitope-blocking antibody, atypical primary immune response Ig subclasses, anamnestic cross-reactive recall and inappropriate $T_{H1}$ and/or $T_{H2}$ cytokine metabolism.

At the immunologic level, very different etiologic agents can yield diverse pathogenesis and disease outcome as observed, for example, with HIV-1 verses human rhinovirus. Highly successful immune system evading strategies, such as, "Deceptive Imprinting," have evolved and are selected and maintained across host and microbial taxa. Thus, the operational failures of the vertebrate immune system, for example, arising from pathogen Deceptive Imprinting, are fundamentally the same whether infected with HIV-1 or with the common cold virus for an average of 2-6 times a year for 60 years.

Although some advances with regard to antigen delivery and expression have improved the immunogenicity of some Class Two microbial pathogens, current vaccine technologies have not readily translated into new, broadly effective and safe, licensed vaccines for use in humans. That may be due, in large part, to a poor understanding of the fundamental laws governing the vertebrate host defense system origin, repertoire development, maintenance, activation, senescence and co-evolution in similar and dissimilar environments.

What is lacking currently in human influenza vaccine development is a composition that induces immunity and protection which is less homotypic and subtype-dependent and would therefore not require the mixing and production of multiple subtypes in the current egg-based technology production scheme year to year. A suitable new product is an influenza recombinant HA or NA subunit vaccine that induces immune responses capable of cross-neutralizing both intra-subtype antigenic variants and hetero-subtypes of influenza virus.

Influenza is a NIAID Category C pathogen and causes 36,000 deaths and 220,000 hospitalizations in the U.S. every year. A respiratory disease, influenza spreads through droplets and/or contaminated fomites from the cough or sneeze of an infected person. Higher risk groups include children and the elderly, and having influenza commonly leads to secondary complications of influenza-related pneumonias, upper respiratory complications (otitis media in children) and other systems diseases (e.g. cardiovascular and so on). Influenza is the source of the worst pandemic in history; the Spanish flu of 1918 caused over 40 million deaths worldwide. In the U.S., the annual direct medical costs (hospitalization, office visits, medication etc.) of influenza are estimated at $4.6 billion. Furthermore, each year, up to 111 million workdays are lost because of influenza with an associated cost to American businesses of more than $7 billion a year in sick days and lost productivity. Total direct and indirect costs (work days lost, school days lost etc.) of a severe influenza epidemic are at least $12 billion per year.

Influenza virus, and when attended by secondary bacterial infections, has long been known to be a cause of excess morbidity and mortality. Complications include pneumonia, bronchitis, congestive heart failure, myocarditis, meningitis, encephalitis and myositis. Some groups of people at high risk for complications are those with chronic pulmonary or cardiovascular disorders, residents of chronic care facilities, including nursing homes, and those persons 85 years and older. (Recommendations of the Advisory Committee on Immunization Practices (ACIP) for Prevention and Control of Influenza. MMWR, 1996, Vol 45; and Thompson et al., JAMA 2003; 289:179-186). The geriatric population in the United Stated has doubled between the years 1976 and 1999, and is expected to rise over the next few years as the post World War II baby boomers age. People in that age bracket are 16 times more likely to die of an influenza-associated disease than are persons aged 65 to 69. Another important contributing factor to the increase of influenza-associated deaths in the 1990's is the predominance of the influenza A (H3N2) virus, a more virulent form of the recently circulating influenza viruses.

Influenza is a single-stranded ribonucleic acid (RNA) virus which mutates rapidly to form new virulent strains. The strains are classified into three groups, influenza A, B and C. The virus is further classified based on two surface glycoproteins, hemagglutinin (HA) and neuraminidase (NA), into at least 16 HA and at least 9 NA subtypes. Recent whole genome analysis of the human influenza virus sponsored by the NIAID/NIH and collected between 1996-2004 from New York State revealed that despite sharing the same HA, multiple, persistent, phylogenetically distinct lineages co-circulate in the same population resulting in reassortment and the generation of antigenically novel clades. While antigenic variance of HA is still the dominant selective pressure on human influenza A virus evolution, the finding that antigenically novel clades emerge by reassortment among persistent viral lineages rather than via antigenic drift is of major significance for the current, dated annual method of influenza vaccine strain selection and production (Holmes et al., PLoS Biol. 2005 3(9):e300). Influenza can be obtained from swine, birds, horses, dogs and other mammals.

At the heart of the problem in the annual global virus tracking programs and subsequent "reactionary" vaccine production that ensues, is the issue of antigenic variation.

Antigenic variation is an evolved mechanism to ensure rapid sequence variation of specific pathogen gene(s) encoding homologues of an individual protein antigen, usually involving multiple, related gene copies, resulting in a change in the structure of an antigen on the surface of the pathogen. Thus, the host immune system during infection or re-infection is less capable of recognizing the pathogen and must make new antibodies to recognize the changed antigens before the host can continue to combat the disease. As a result, the host cannot stay completely immune to the viral disease. That phenomenon stands as one of the more, if not, most formidable problem challenging modern vaccine development today.

Not surprisingly, the immune response generated after infection or vaccination with all currently licensed vaccines is highly subtype and strain specific. In practice, that means antibodies elicited during natural, experimental infection and vaccination are only capable of neutralizing the homologous virus. The subtype/strain-specific humoral immune response appears to be due to the relative immunodominance of various antigenic sites found on the globular head of the hemagglutinin molecule (Wiley et al., Nature, 1981; 289:373-378). More specifically, the antibody response has been mapped to five major antigenic sites within the globular head of the HA. Of the five HA epitopes (A-E), two sites, A and B, are the most immunodominant and also were associated with the highest amount of amino acid hypervariability, due, in part, to reoccurring point mutations, deletions and occasional introduction of N-linked glycosylation sites, known collectively as the "antigenic drift" of the virus (Cox & Bender, Semin. Virol. 1995; 6:359-70; Busch et al., Sci. 286:1921, 1999; Plotkin & Dushoff, PNAS 100:7152, 2003; and Munoz & Deem, Vaccine 23, 1144, 2005).

Original antigenic sin, first described in 1953 by Francis (Ann. Int. Med., 1953, 399:203), is a primary immune response, that when boosted not by the homologous, but by a cross-reacting vaccine or incoming viral subtype/strain, results in the newly formed antibodies reacting better with the previous antigen than with the incoming antigen.

The loss of immune specificity directed by that aleatory recall poses a real problem for the host immune system to mount equal and potent humoral responses to the changing virus both during an infection and between infections. Thus, it is not surprising that natural infection and vaccination fail to yield a more functional cross-reactive primary and anamnestic immunity as the repertoire development against those less immunogenic epitopes, which may be most conserved and capable of generating cross-strain immunity, are lower on the antigenic hierarchy. The immunologic phenomenon whereby immunodominant epitopes misdirect the immune response away from more conserved and less immunogenic regions on an antigen was initially termed, "clonal dominance" (Kohler et al., J Acquir. Immune Defic. Syndr. 1992; 5:1158-68), which later was renamed as, "Deceptive Imprinting" (Köhler et al., Immunol. Today 1994 (10):475-8).

The immunologic mechanisms for immunodominance behind deceptive imprinting are not fully understood, and no one mechanism yet fully explains how or why certain epitopes have evolved to be immunoregulatory and immunodominant. The range of immune responses observed in the phenomenon include the induction of highly strain/isolate-specific neutralizing antibody capable of inducing passive protection in experimental animal model-viral challenge systems all the way to the induction of a binding non-protective/non-neutralizing, blocking and even pathogenenhancing antibody that, in some cases, prevents the host immune system from recognizing nearby adjacent epitopes to interfering with $CD_4$ T cell help. The same decoying of the immune response through immunodominance resulting in a more narrowly focused set of epitopes is observed with T cells of the host helper and cytotoxic cell-mediated immunity (Gzyl et al., Virology 2004; 318(2):493-506; Kiszka et al., J. Virol. 2002 76(9):4222-32; and Goulder et al., J. Virol. 2000; 74(12):5679-90).

Vaccination is the best way to prevent the disease and the current trivalent killed virus and modified live (attenuated) influenza vaccines are developed every year based on worldwide epidemiological surveillance of active viral strains. Both vaccines contain influenza A and influenza B subtypes. The licensed influenza vaccines consist of inactivated whole or chemically split subunit preparations from two influenza A subtypes (H1N1 and H3N2) and one influenza B subtype. Production of influenza vaccines involves the adaptation of the selected variants for high yield in eggs by serial passage or reassortment with other high-yield strains. Selected influenza viruses are grown in chicken eggs, and the influenza virions purified from allantoic fluid. Whole or split virus preparations are then killed by treatment with an inactivating agent, such as formalin. More than 90% of the United States market for the vaccine is served by two companies, Aventis Pasteur with more than 50% market share and Chiron (PowderJect) (U.K.). An intranasal vaccine, FluMist®, was approved and first sold in 2003.

Limitations of the currently available influenza vaccines include:

(1) Reduced efficacy in the elderly. Among the elderly, the rate of protection against illness is lower, especially for those who are institutionalized (Gorse et al., J. Infec. Dis. 190: 11-19, 2004). Significant antibody responses to a trivalent subvirion influenza vaccine were observed in less than 30 percent of subjects 65 years of age or older (Powers & Belshe, J. Infec. Dis. 167:584-592, 1993);

(2) Production in eggs. The current manufacturing process is dependent on chicken eggs. Influenza virus strains must replicate well in eggs and a large supply of eggs is required each year. Production is at risk each year because of the need to find a suitable virus combination;

(3) Inability to respond to late appearing and drift strains, such as A/Sydney/5/97 in the late nineties, or to respond to a potential pandemic strain, such as the Hong Kong H5N1 virus that appeared in 1997;

(4) Protection with current whole or split influenza vaccines is short-lived, and effectiveness wanes as genetic changes occur in the epidemic strains of influenza due to antigenic variation. Ideally, the vaccine strains are matched to the influenza virus strains causing disease. Changes can occur in the hemagglutinin of egg-grown influenza virus when compared to primary isolates from infected individuals (Oxford et al., J. Gen. Virol. 72:185-189, 1989; and Rocha et al., J. Gen. Virol. 74:2513-2518, 1993) reducing the potential effectiveness of the vaccine;

(5) The side effect of having the vaccine produced in eggs for those allergic to eggs; and (6) The current licensed manufacturing system yields one vaccine per chicken egg infected with the influenza virus and the production time is approximately 24 weeks.

Thus, the current licensed influenza vaccines do not: (1) induce antibodies capable of neutralizing the common annually recurring antigenic variants circulating during an epidemic, as well as the sub-type viruses and reassortment viruses; (2) illicit a strong immune response in the elderly;

and (3) find wide applicability due to side effects, for example, some vaccines cannot be administered to children.

SUMMARY

The disclosure relates, in part, to novel influenza antigens with enhanced or novel immunogenicity. An influenza composition of interest can serve as an improved vaccine, resulting from modifications providing the virus or viral subunit antigen with a different array of and/or newly recognizable epitopes.

The more efficient and rapid use of recombinant technology coupled to a novel immune refocusing technology resulting in subunit HA, NA or both, and/or compositions containing same greatly change the current practice of vaccine development by generating an influenza vaccine with improved cross-strain effectiveness, thereby obviating the need for the current practice of global annual tracking of the virus, which will save millions of dollars, diverted medical resources, including the time and labor of the annual scale-up for production and manufacturing in eggs, as well as human lives.

Additional features and advantages are described herein, and will be apparent from the following Drawings and Detailed Description.

BRIEF DESCRIPTION OF THE DRAWINGS

The following drawing is provided to exemplify various aspects of the instant disclosure and is in no way to be interpreted as limiting the scope of the disclosure of interest.

FIG. 1 depicts Table 1 relating to the results of testing immune refocused HA antigens.

FIG. 2 depicts Table 2 relating to particular mutations and the sequences (SEQ ID NOs:44-77, respectively, in order of appearance) thereof.

FIG. 3 depicts the approximate location of a set of examples of immune refocusing mutations on H1N1 HA. Panel A depicts the structure of the HA trimer comprising three HA-1 and HA-2 chains. Panels B, C and D depict HA monomers showing amino acids in approximate locations of selected mutations. The figures were adapted from the structural file, 1RU7.pdb, of the H1N1 HA of influenza, (A/PR8/1934, Gamblin et al., Science, 303:1838-1842, 2004), which also can be found in the RCSB Protein Data Bank.

FIG. 4 depicts Table 3 which provides combination mutations in 2 and 3 epitopes.

FIG. 5 depicts Table 4 which provides combination mutations in 5 epitopes.

DETAILED DESCRIPTION

Influenza is defined herein as virus that includes types A, B and C. The virus can be found in birds and a variety of mammals, such as, cats, dogs, horses, hogs and so on. Type A is the most virulent in humans and can result in either seasonal epidemics or occasionally and more rarely, more fatal pandemic episodes. The types are defined by a number of serotypes, which is a reflection of the host immune response to antigens expressed on the virus particle surface. Two structures on the virus surface that carry the majority of epitopes correlated with vaccine protection are a hemagglutinin (HA or H) and a neuraminidase (NA or N). There are at least 16 known H subtypes and at least 9 known N subtypes. HA mediates virus attachment and fusion. NA possesses sialidase activity.

"Wild type" refers to a naturally occurring organism or portions thereof. The term also relates to nucleic acids and proteins found in a naturally occurring organism of a naturally occurring population arising from natural processes, such as seen in polymorphisms arising from natural mutation and maintained by genetic drift, natural selection and so on, and does not include a nucleic acid or protein with a sequence obtained by, for example, recombinant means.

"Immunogen" and "antigen" are used interchangeably herein as a molecule that elicits a specific immune response of antibody (humoral-mediated) and/or T cell origin (cell-mediated), for example, containing an antibody that binds to that molecule or a $CD_4^+$ or $CD_8^+$ T cell that recognizes a cell expressing that molecule, such as, a virally infected cell. That molecule can contain one or more sites to which a specific antibody or T cell binds. As known in the art, such sites are known as epitopes or determinants. An antigen can be polypeptide, polynucleotide, polysaccharide, a lipid and so on, as well as a combination thereof, such as a glycoprotein or a lipoprotein. An immunogenic compound or product, or an antigenic compound or product is one which elicits a specific immune response, which can be humoral, cellular or both.

A vaccine is an immunogen or antigen used to generate an immunoprotective response, that is, the response, such as, antibody, reduces the negative impact of the immunogen or antigen, or entity expressing same, in a host. The dosage is derived, extrapolated and/or determined from preclinical and clinical studies, as known in the art. Multiple doses can be administered as known in the art, and as needed to ensure a prolonged prophylactic or non-reactive state. The successful endpoint of the utility of a vaccine for the purpose of the instant disclosure is the resulting presence of an induced immune response in a host (e.g. humoral and/or T cell-mediated) resulting, for example, in the production of serum antibody, or antibody made by the host in any tissue or organ, that binds the antigen or immunogen of interest. In some embodiments, the induced antibody in some way combines with a compound, molecule and the like carrying the cognate antigen or immunogen, or directs the host to neutralize, reduce, prevent and/or eliminate a pathogen from infecting and/or causing clinical disease. That immune response can be monitored practicing methods known in the art, such as, an ELISA, Western blot and so on. Immunoprotection for the purposes of the instant disclosure is the presence of such anti-pathogen, anti-immunogen, anti-viral and the like immune response (e.g. antibody and/or T cell that binds the immunogen or infected cell) in an exposed host. That can be determined using any known immunoassay, such as, an ELISA and/or hemagglutinin inhibition assay. Alternatively, one can use a viral neutralization assay to ascertain presence of, for example, circulating neutralizing anti-viral antibody. For the purposes of the instant disclosure, observing immunoprotection in a host, that is, presence of a circulating anti-influenza antibody, of at least seven days, at least fourteen days, at least seventeen days, at least twenty-one days, at least thirty days or more is evidence of efficacy of a vaccine of interest. Alternatively, in general, a hemagglutination inhibition (HI) titer of approximately 1:40 against the homologous single strain of influenza used to make the vaccine can be an endpoint that signals a candidate vaccine is obtained. In an animal model, any delay in lethality following exposure can be evidence of protection for the purposes of the disclosure. Thus, in the case of mice exposed to pathogenic strains of influenza, often the first mice can succumb at about day 10 following exposure. Thus, if the first day an exposed mouse succumbs is extended at least one day, at least two days, at least three days or more is considered protection for the purposes of the instant disclosure. The time of immunoprotection can be at least 14 days, at least 21 days, at least 28 days, at least 35 days, at least 45 days, at least 60 days, at least 3 months, at least 4 months, at least 5 months, at least 6 months, at least 1 year, at least 2 years or longer. Preferably the immunoprotection is observed in outbred populations, and to different forms, subtypes, strains, variants, alleles and the like of a pathogen. The composition of interest can comprise virus particles, inactivated or attenuated (modified live) or a subunit of the virus, such as, for example, NA or HA. The composition also can comprise a virus-like particle (VLP), which is known in the art as a structure that expresses virus proteins and antigens as found on an intact replicating virion, but in the context of the instant disclosure, expressing an immunodampened immunodominant epitope. Normally, VLP's lack virus nucleic acid or portion thereof that enables nucleic acid replication, thereby making a VLP, non-infectious.

In another embodiment, an antigen, a determinant or portion thereof can be cloned into the genome of a wild-type virus, replacing the homologous wild type gene(s). The recombinant virus then is the same as a wild type virus save the immunodampened molecule. That virus can be influenza or another virus carrier. Thus, for example, a strain of influenza virus which propagates well in eggs can be manipulated to express an immunodampened molecule, and that recombinant virus can be propagated using the existing materials and methods of vaccine production using eggs to yield an immunodampened vaccine. The vaccine can be tailored to generate an immune response to one antigen, two antigens or more; to one virus, to two separate lines, strains, clades and so on of virus or more; to one epitope, two epitopes or more; to one serotype, two serotypes or more; and so on. That can be obtained by including plural components, compositions, viruses, VLP's and so on wherein one of said components, compositions, viruses, VLP's and so on expresses an immunodampened antigen of interest which can generate a response to plural HA types, NA types or both. Alternatively, the plural elements can be joined in a single multifunctional composition.

"Immunodominant epitope" is an epitope that selectively provokes an immune response in a host to the effective or functional exclusion, which may be partial or complete, of other epitopes on and of that antigen.

"To immunodampen an epitope" is to modify an epitope to substantially prevent the immune system of the host from producing antibodies, helper or cytotoxic T cells against that epitope. However, immunodampen does not necessarily result in the complete removal of said epitope or reactivity to that epitope.

Immune refocusing (IR) or immune refocusing technology (IRT) can be used to create effective vaccines against pathogens expressing immunodominant epitopes. The technique is applied most appropriately in organisms that have evolved a strategy known as Deceptive Imprinting to evade the host immune response, for example, by having an immunodominant epitope that displays a high level of antigenic drift. Such an immunodominant epitope ordinarily takes the form of a plurality of amino acids that can be changed without affecting the survivability of the pathogenic organism. Immune refocusing is synonymous of immunodampen.

Immunodampening of an immunodominant epitope of an antigen can result in the production in a host organism of high titer antibodies or T cell responses against non-dominant epitopes on that antigen and/or new titers of antibodies or T cell responses to otherwise relatively immune silent epitopes. Such immunodampened antigens can serve as effective vaccines against organisms that have an antigen with a moderately or highly variable and/or conserved immunodominant epitope(s). The antibodies raised to such immunodominant epitopes or antigens can serve as effective vaccines against cognate organisms.

An immunodominant epitope can be identified by examining serum or T cell reactivity from a host organism infected with the pathogenic organism. The serum is evaluated for content of antibodies that bind to the identified antigens that are likely to cause an immune response in a host organism. If an immunodominant epitope is present, substantially many antibodies in the serum will bind to the immunodominant epitope, with little or no binding to other epitopes present on or in the antigen.

After an immunodominant epitope has been identified, the immunodominant epitope is immunodampened as taught herein using the materials and methods taught herein and as known in the art as a design choice. Such manipulations can be made at the nucleic acid level, at the level of the protein, at the level of a carbohydrate and so on, or combinations thereof, practicing methods taught herein and known in the art.

For example, the presence of N-linked carbohydrate (CHO) can be determined by the primary amino acid sequence of the polypeptide. A triplet amino acid sequence consisting of asparagine, followed by any amino acid, and ending with a serine or threonine (N-X-S/T), where X is any amino acid other than proline or aspartic acid, is a target for N-linked CHO addition. An N-linked glycosylation site can be added or removed from an epitope practicing methods and materials known in the art.

For example, a recombinant gp120 of HIV that displays a molecularly introduced N-linked sequon (NXT/S), which resulted in the addition of a supernumerary N-linked glycan in the immunodominant V3 domain, exhibited novel antigenic properties, such as the inability to bind antibodies that recognize wild type V3 epitopes while inducing antibody responses to other previously silent or less immunogenic epitopes. Presence of the supernumerary carbohydrate moiety did not compromise the infectious viability of the HIV-1 recombinant virus. Test animals immunized with the recombinant glycoprotein showed moderate to high titers of antibodies that neutralize infection to both homologous and heterologous wildtype HIV-1 in vitro. Thus, immunodampening of the immunodominant epitope within the V3 domain of gp120/160 caused the immune response to refocus on other neutralizing epitopes that are located on the same antigen, see U.S. Pat. Nos. 5,585,250 and 5,853,724.

Alternatively, a particular amino acid of the immunodominant epitope can be replaced, substituted or deleted to dampen immunogenicity. Immunodampening can occur by replacing, substituting or deleting one amino acid, two amino acids, three amino acids or more of the immunodominant epitope, for example, by site-directed mutagenesis of the nucleic acid encoding the antigen. Methods for altering nucleic acids and/or polypeptides are provided herein, and are known in the art.

Immunodampening can be affected by any of a variety of techniques such as, altering, substituting or deleting specific amino acids of the epitope, or adding, for example, a glycosylation site at or near the epitope. As taught herein, the changes can be effected at the level of the polypeptide or at the level of the polynucleotide, practicing methods known in the art. Thus, a polypeptide can be altered by adding, deleting or substituting one or more molecules, groups, compounds and the like to a target site on or in an epitope. For example, a particular amino acid can be derivatized chemically or can be modified to carry an extra group, such as a polysaccharide, such as, polyethylene glycol.

Following manipulation of immunogenic structures, a screening analysis of binding of the mutein (that is, the manipulated antigen of interest, that is, the immunodampened antigen of interest) to defined, known antibody that binds to one or more immunodominant epitopes of influenza can be used to determine whether immunodampening occurred. For example, a polypeptide can be synthesized to contain one or more changes to the primary amino acid sequence of the immunodominant epitope. Alternatively, the nucleic acid sequence of the immunodominant epitope can be modified to express an immunodampened epitope. Hence, the nucleic acid sequence can be modified by, for example, site-directed mutagenesis to express amino acid substitutions, insertions, deletions and the like, some of which may introduce further modification at or near the immunodominant epitope, such as, introducing a glycosylation site, such as, mutations which cause N-glycosylation or O-glycosylation at or near the immunodominant epitope and so on.

Hence, a nucleic acid of interest encoding one or more immunodampened epitopes in a polypeptide of interest can be placed in a cloning and/or expression vector practicing materials and methods as known in the art and generally commercially available as a design choice. For example, plasmids, cosmids, viruses, replicons and so on can be used, again, many are commercially available. Viral vectors include those obtained from adenovirus, AAV, alpha viruses, phage and so on. Influenza also can be used. Suitable host cells for propagating the vector of interest are known and include prokaryotic cells, eukaryotic cells, bacteria, insect cells, mammal cells and so on. The cells can be configured to secrete the recombinant protein of interest. That polypeptide can be purified and used as an immunogen.

Alternatively, the polypeptide can be inserted into a vector comprising an influenza genome or an influenza virus, generally replacing the homologous encoding sequence from which the polypeptide was derived to enable expression of the immune refocused polypeptide on said influenza virus, virus-like particle or structure, virus surface structure component, subunit and so on.

Hence, the immune refocusing technology is independent of vector technology and can be applied to multiple expression systems. Accordingly, the immune refocused antigens can be incorporated into a number of currently utilized and novel vaccine vectors including, but not restricted to: 1) recombinant influenza viruses to be produced using currently acceptable technologies such as in cultured mammalian cells or chicken embryos; 2) recombinant temperature-sensitive influenza viruses such as Flu-Mist; 3) split vaccines; 4) subunit vaccines expressed in insect, mammalian, yeast, bacterial, or other cells; 5) DNA expression plasmids; and 6) heterologous viral expression systems, such as, recombinant vaccinia virus, adenovirus, lentivirus, and the like.

Multiple methods for the purification of immunogens containing the immune refocused HA antigens are known to the art. Recombinant viruses incorporating the immune refocused HA antigens are purified using established and approved techniques currently used in the preparation of licensed vaccines.

Subunit vaccines produced in insect, mammalian or other in vitro expression system can be purified using conventional chromatographies, separations and purifications such as ion exchange, lectin-binding resins, size fractionations, antibody affinity and the like. In addition, the immunogens can be expressed with fusion domains designed to facilitate purification. For example, HA antigens can be expressed as, for example, polyhistidine fusions to permit rapid and simplified purification on metal-activated resins. Such fusion partners can be removed by specific proteolytic cleavage using methods known to the art, if so desired.

One procedure for obtaining epitope muteins (a mutant epitope that varies from wild type) and the like is "alanine scanning mutagenesis" (Cunningham & Wells, Science 244: 1081-1085 (1989); and Cunningham & Wells, Proc. Natl. Acad. Sci. USA 84:6434-6437 (1991)). One or more residues are replaced by alanine (Ala) or polyalanine residue(s). Those residues demonstrating functional sensitivity to the substitutions then can be refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues. In addition, a substituted amino acid may be selected based on, for example, size, shape or other parameter of the replaced amino acid. For example, glutamine may be substituted for glutamic acid to reduce the charge of an epitope with minimal change in size and shape.

A more systematic method for identifying amino acid residues to modify comprises identifying residues involved in immune system stimulation or immunodominant antibody recognition and those residues with little or no involvement with immune system stimulation or immunodominant antibody recognition. An alanine scan of the involved residues is performed, with each Ala mutant tested for reducing immune system stimulation to an immunodominant epitope or immunodominant antibody recognition. In another embodiment, those residues with little or no involvement in immune system stimulation are selected to be modified. Modification can involve deletion of one or more residues, substitution of a residue or insertion of one or more residues adjacent to a residue of interest. In one embodiment, the modification involves substitution of the residue by another amino acid. A conservative substitution can be a first substitution. If such a substitution results in inducing immune system stimulation or increased reactivity with known immunodominant antibody, then another conservative substitution can be made to determine if more substantial changes are obtained.

Even more substantial modification in the ability to alter the immune system response away from the immunodominant epitope can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

For example, the naturally occurring amino acids can be divided into groups based on common side chain properties:

(1) hydrophobic: methionine (M or Met), alanine (A or Ala), valine (V or Val), leucine (L or Leu) and isoleucine (I or Ile);

(2) neutral, hydrophilic: cysteine (C or Cys), serine (S or Ser), threonine (T or Thr), asparagine (N or Asn) and glutamine (Q or Gln);

(3) acidic: aspartic acid (D or Asp) and glutamic acid (E or Glu);

(4) basic: histidine (H or His), lysine (K or Lys) and arginine (R or Arg);

(5) residues that influence chain orientation: glycine (G or Gly) and proline (P or Pro), and (6) aromatic: tryptophan (W or Trp), tyrosine (Y or Tyr) and phenylalanine (F or Phe).

Non-conservative substitutions can entail exchanging an amino acid with an amino acid from another group. Conservative substitutions can entail exchange of one amino acid for another from within a group.

Preferred amino acid substitutions are those which dampen an immunodominant epitope, but can also include those which, for example: (1) reduce susceptibility to proteolysis, (2) reduce susceptibility to oxidation, (3) alter immune system stimulating activity and/or (4) confer or modify other physico-chemical or functional properties of such analogs. Analogs can include various muteins of a sequence other than the naturally occurring peptide sequence. For example, single or multiple amino acid substitutions (such as, conservative amino acid substitutions) may be made in the naturally occurring or mutein sequence. A conservative amino acid substitution generally should not substantially change the structural characteristics of the parent sequence (e.g., a replacement amino acid should not tend to break a helix that occurs in the parent or mutein sequence, or disrupt other types of secondary structure that characterizes the parent sequence) unless for a change in the bulk or conformation of the R group or side chain (Proteins, Structures and Molecular Principles (Creighton, ed., W. H. Freeman and Company, New York (1984); Introduction to Protein Structure, Branden & Tooze, eds., Garland Publishing, New York, N.Y. (1991)); and Thornton et al. Nature 354:105 (1991)).

Ordinarily, the epitope mutant with altered biological properties will have an amino acid sequence having at least 75% amino acid sequence identity or similarity with the amino acid sequence of the parent molecule, at least 80%, at least 85%, at least 90% and often at least 95% identity. Identity or similarity with respect to parent amino acid sequence is defined herein as the percentage of amino acid residues in the candidate sequence that are identical (i.e., same residue) or similar (i.e., amino acid residue from the same group based on common side-chain properties, supra) with the parent molecule residues, after aligning the sequences and introducing gaps, if necessary, to achieve the maximum percent sequence identity.

Covalent modifications of the molecules of interest are included within the scope of the disclosure, for example, to immunodampen a molecule or to obtain a functional equivalent that may or may not carry enhanced, additional or different features or properties, exclusive of immunodampening. Such may be made by chemical synthesis or by enzymatic or chemical cleavage of the molecule, if applicable. Other types of covalent modifications of the molecule can be introduced into the molecule by reacting targeted amino acid residues of the molecule with an organic derivatizing agent that is capable of reacting with selected side chains or with the N-terminal or C-terminal residue.

Also, various organic chemistry materials and methods can be practiced to modify a component of an epitope. For example, WO05/35726 teaches various methods for introducing, modifying, changing, replacing and so on substituents found on biomolecules.

For example, cysteinyl residues can be reacted with α-haloacetates (and corresponding amines), such as chloroacetic acid or chloroacetamide, to yield carboxylmethyl or carboxyamidomethyl derivatives. Cysteinyl residues also can be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercura-4-nitrophenol or chloro-7-nitrobenzo-2-oxa-1,3-diazole, for example.

Histidyl residues can be derivatized by reaction with diethylpyrocarbonate at pH 5.5-7.0. p-bromophenacyl bromide also can be used, the reaction is preferably performed in 0.1 M sodium cacodylate at pH 6.0.

Lysinyl and a amino terminal residues can be reacted with succinic or other carboxylic acid anhydrides to reverse the charge of the residues. Other suitable reagents for derivatizing α-amino-containing residues include imidoesters, such as, methyl picolinimidate, pyridoxal phosphate, pyridoxal, chloroborohydride, trinitrobenzenesulfonic acid, O-methylisourea and 2,4-pentanedione, and the amino acid can be transaminase-catalyzed with glyoxylate.

Arginyl residues can be modified by reaction with one or several conventional reagents, such as, phenylglyoxal, 2,3-butanedione, 1,2-cyclohexanedione and ninhydrin. Derivatization of arginine residues often requires alkaline reaction conditions. Furthermore, the reagents may react with lysine as well as the arginine c amino group.

The specific modification of tyrosyl residues can be made with aromatic diazonium compounds or tetranitromethane. For example, N-acetylimidizole and tetranitromethane can be used to form O-acetyl tyrosyl species and 3-nitro derivatives, respectively.

Carboxyl side groups (aspartyl or glutamyl) can be modified by reaction with carbodiimides (R—N═C═C—R'), where R and R' can be different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonium ions.

Glutaminyl and asparaginyl residues are frequently deamidated to the corresponding glutamyl and aspartyl residues, respectively, under neutral or basic conditions. The deamidated form of those residues falls within the scope of the disclosure.

Other modifications include hydroxylation of proline and lysine, phosphorylation of hydroxyl groups of serinyl or threonyl residues, methylation of the a amino groups of lysine, arginine and histidine (Creighton, Proteins: Structure and Molecular Properties, W.H. Freeman & Co., San Francisco, pp. 79-86 (1983)), and acetylation of the N-terminal amine and amidation of any C-terminal carboxyl group.

Another type of covalent modification involves chemically or enzymatically coupling glycosides, sugars, saccharides and the like to the molecules of interest. Depending on the coupling mode used, the sugar(s) may be attached to: (a) arginine and histidine; (b) free carboxyl groups; (c) free sulfhydryl groups, such as those of cysteine; (d) free hydroxyl groups, such as those of serine, threonine or hydroxyproline; (e) aromatic residues such as those of phenylalanine, tyrosine or tryptophan; or (f) the amide group of glutamine. Such methods are described in WO 87/05330 and in Aplin & Wriston, CRC Crit. Rev. Biochem., pp. 259-306 (1981). Sugar residues also can be added enzymatically using, for example, a glucosyl transferase, a sialyl transferase, a galactosyl transferase and so on.

Removal of any carbohydrate moieties present on the molecule of interest may be accomplished chemically or enzymatically. Chemical deglycosylation, for example, can require exposure of the molecule to the compound, trifluoromethanesulfonic acid, or an equivalent compound, resulting in cleavage of most or all sugars except the linking sugar (N-acetylglucosamine or N-acetylgalactosamine), while leaving the remainder of the molecule intact. Chemical deglycosylation is described, for example, in Hakimuddin et al., Arch. Biochem. Biophys. 259:52 (1987) and in Edge et al., Anal. Biochem. 118:131 (1981). Enzymatic cleavage of carbohydrate moieties on molecules can be achieved by any of a variety of endoglycosidases and exoglycosidases as described, for example, in Thotakura et al., Meth. Enzymol. 138:350(1987). Thus, a mannosidase, a fucosidase, glucosaminosidase, a galactosidase and so on can be used.

RNA or DNA encoding the HA, NA and the like of influenza is readily isolated and sequenced using conventional procedures (e.g., by using oligonucleotide probes that are capable of binding specifically to the relevant genes, Innis et al. in PCR Protocols. A Guide to Methods and Applications, Academic (1990) and Sanger et al., Proc. Natl. Acad. Sci. 74:5463 (1977)). Once isolated, the DNA may be placed into expression vectors, which then are placed into host cells, such as, *E. coli* cells, NSO cells, COS cells, Chinese hamster ovary (CHO) cells or myeloma cells, to obtain synthesis of the protein of interest in the recombinant host cells. The RNA or DNA also may be modified, for example, by substituting bases to optimize for codon usage in a particular host cell or by covalently joining to the coding sequence of a heterologous polypeptide.

Thus, as taught herein, a polynucleotide of interest encoding and expressing one or more immunodampened epitopes can be expressed practicing molecular biology and recombinant materials and methods as known in the art to obtain a source of recombinant polypeptide of interest.

In another embodiment, a polynucleotide of interest encoding one or more immunodampened epitopes can replace the homologous wild type sequence in an influenza genome to yield a virus, a virus-like structure or subunit thereof that expresses the one or more immunodampened epitopes. Hence, that virus strain can be propagated using standard techniques, such as the currently used egg-based technology, to generate an immunogen, which can be used alone as a vaccine or can be combined with other active agents, such as, an unmodified virus or a plurality of viruses, for example, to simulate the current bivalent and trivalent vaccines.

The phrases and terms, as well as combinations thereof, "functional fragment, portion, variant, derivative or analog" and the like, as well as forms thereof, of an influenza virus, antigen, component, subunit, HA, NA and the like thereof relate to an element having qualitative biological activity in common with the wild type or parental element or the original non-immunodampened antigen from which the variant, derivative, analog and the like was derived. For example, a functional portion, fragment or analog of HA is one which stimulates an immune response as does native HA, although the response may be to a different epitope on the HA.

Thus, included within the scope of the disclosure are functional equivalents of a virus, or portion or derivative thereof, of interest. The term "functional equivalents" includes the virus and portions thereof with the ability to stimulate an immune response to influenza.

Hence, once a candidate immunodampened polypeptide is identified, it is well within the skill of the artisan to make modifications to that amino acid sequence while maintaining the goals of immunodampening and uncovering previously silent epitopes. Thus, for example, the encoding nucleic acid can be modified to encode amino acid insertions, deletions or substitutions that do no adversely impact the two goals referred to herein. In another embodiment, the amino acids are modified, derivatized, substituted and so on practicing materials and methods known in the art so long as the two goals referred to herein are not adversely impacted. As taught herein, such changes and modifications from the original immunodampened polypeptide are considered functional equivalents thereof. The degree of immunodampening can be quantified in an in vitro or animal assay as taught herein or as known in the art. Similarly, the degree of enabling a response to previously silent epitopes can be quantified in an in vitro or animal assay as taught herein or as known in the art. When a modification is made to the original immunodampened sequence, the degree of acceptable reduction in the degree of one of the two goals taught herein is a design choice. Generally, a reduction of no more than 25% of reactivity is tolerated because normally, the desire is to have as little reaction to the immunodominant epitopes as possible. Hence, if a modification to the original immunodampened sequence reveals, for example, a return of 25% of reactivity thereto as determined, for example, in an ELISA using an antibody to that immunodominant epitope as compared to no reactivity in the original immunodampened epitope, that could be considered an acceptable reduction in reactivity for a functional equivalent. It may be that no more than a 20% reduction, no more than a 15% reduction, no more than a 10% reduction, no more than a 5% reduction or no reduction is considered acceptable for a functional equivalent of an immunodampened antigen. Similarly, with regard to now reactivity to previously silent epitopes, a reduction of no more than 25% is tolerated because normally, the desire is to have as much reaction to the previously silent epitopes as possible. Hence, if a modification to the original immunodampened sequence reveals, for example, a loss of 25% of reactivity to the previously silent epitope as determined, for example, in an ELISA using an antibody that was raised to the previously silent epitope as compared to maximal reactivity in the original immunodampened epitope, that could be considered an acceptable reduction in reactivity for a functional equivalent. It may be that no more than a 20% reduction, no more than a 15% reduction, no more than a 10% reduction, no more than a 5% reduction or no reduction is considered acceptable for a functional equivalent of an antigen expressing previously silent epitopes.

Parts of an influenza virus of interest, such as membrane or non-membrane preparations carrying HA, NA, M2 or combinations, as well as preparations of any other influenza antigens, can be obtained practicing methods known in the art. When one or more immunodominant non-protective epitopes (IDNPEs, which also include epitopes that stimulate strain-specific, but less broad immunity) are removed or dampened, for example, by intramolecular modifications (e.g. deletions, charge changes, adding one or more N-linked sequons and so on) and given as an antigen to a naive animal, the changes to the IDNPE can induce a new hierarchy of immune responses at either or both the B and T cell levels (Garrity et. al., J. Immunol. (1997) 159(0:279-89) against subdominant or previously silent epitopes. That technology as described herein is known as, "Immune Refocusing."

Once a change is made, whether the change alters, such as, reduces the reactivity of the immunodominant epitope now modified, the, "dampened epitope, antigen and so on," is determined as taught herein or as known in the art. That can be tested in vitro by determining the reactivity of the dampened antigen with defined antisera known to react with that dominant epitope, such as by an ELISA or Western blot, for example. Candidates demonstrating reduced reactivity with those defined antisera are chosen for testing in vivo to determine whether those dampened antigens are immunogenic and the host generates an immune response thereto. Hence, for example, a mouse is immunized to the dampened antigen as known in the art, serum obtained and tested in an in vitro assay for reactivity therewith. That antiserum then can be tested on wild type virus to determine if the antibody still recognizes the wild type epitope or the wild type antigen. That can be done, for example, in an ELISA or a Western blot. The latter can be informative, revealing whether the particular immunodominant epitope is bound, and if the antiserum remains reactive with influenza, the size and possibly, the identity of the molecule carrying the epitope reactive with the mouse antiserum.

Immune refocused vaccine candidates are designed to fold correctly and to adopt native-like conformational epitopes for stimulation of appropriate immune responses. Prior to antigenic testing, it is customary to assess the ability of purified HA antigens to bind conformationally-dependent antibodies and virus receptors on cell surfaces. Methods to assess such interactions are well known in the art and are widely available.

Prior to development of immune refocused antigens as commercial vaccines, non-clinical studies are frequently required. In one method, animals such as mice, guinea pigs, rabbits, chickens, rats, ferrets, etc. are injected or otherwise immunized with the immune refocused vaccine candidates. Following immunization, the panel of immune sera is assessed for multiple activities including reactivity to purified antigen or virus (binding activity), hemagglutination inhibition (inhibition of virus-receptor interactions, HI) and virus neutralization (inhibition of infection of cultured cells and/or inhibition of replication in cultured cells, VN). Methods for assessing sero reactivities are well known to the art.

A comparison of heterologous HI and VN activities of sera from animals immunized with immune refocused antigen with sera from animals immunized with unmutated antigen is used to assess broadening of and improvements to protective immunity. Thus, HI and VN assays are conducted against heterologous strains of H1N1 or other serotypes of influenza virus with the various immune sera raised in the antigenicity study. An increase in the HI or VN titer of a test serum relative to sera from unmodified antigen immunization indicates that the antigen used to raise said test sera stimulates broadened and improved immunity.

To further exemplify the paradigm of analyzing the selection of a vaccine candidate of interest, a hypothetic data set is provided in Table 1 of FIG. 1. Immune refocused HA antigens (Mut H1, Mut H2, Mut H3 and Mut H4) were derived from the A/California/04/2009 strain and are tested for antiviral activities against homologous and heterologous virus. Heterologous viruses (strains 2-4) are presented in order of increasing antigenic divergence from the parental California/04/2009 (Cal/04/09) strain. All immunogens stimulated HI and VN titers equivalent to those induced by unmodified antigen (WT-HA). Sera from Mut-H1 contain statistically higher levels of antiviral activities against strains 2-4 compared to the titers from the WT-HA as determined by both assays. Sera from Mut-H2 and Mut-H3 have 2-fold higher titers of HI and VN activity against strain 2, but that may not be statistically significant if the serum dilution series are done in 2-fold dilutions. However, sera from Mut-H2 and Mut-H3 do have significantly higher HI and VN titers against more highly divergent strains 3 and 4. Analysis of the data shown in Table 1 suggests that Mut-H1 or Mut-H2 stimulate the highest levels of antiviral activities normally measured as correlates in influenza pre-clinical trials.

Additional animal model studies can be performed to further assess protective immunity of immune refocused antigen candidates. In one example of such as test, groups of ferrets are immunized with unmodified antigen or a leading immune refocused candidate (e.g., Mut-H2 presented in Table 1). After immunization, the two groups of ferrets are divided into subgroups and each subgroup is inoculated (challenged) with virus from either homologous or heterologous strains of influenza such as those referred to in Table 1. Measurements of disease, pathogenesis and virus replication are collected during the two weeks following challenge. Analysis of the measurements showing that the ferrets immunized with Mut-H2 and challenged with heterologous strain have reduced disease and virus replication compared with the groups immunized with WT-HA indicate that Mut-H2 stimulates broadened immunity and is an improved vaccine candidate.

Those candidate immunodampened antigens less or no longer reactive with known antisera that bind to the parent immunodominant antigen, yet remain immunogenic in hosts are selected as candidate vaccines for further testing. Candidates may also stimulate enhanced reactivity to the parental immunodominant antigen, while targeting immune refocused epitopes for immune recognition. For example, the mouse antiserum thereto can be tested for reactivity with a number of influenza strains in standardized anti-viral-based assays to determine how generic the reactivity of that antibody is, that is, whether the newly recognized epitopes on the dampened antigen are generic to a wider range of influenza strains and if the antibody has broad antiviral activity.

Thus, a recombinant HA (rHA) subunit protein vaccine can be sufficient to protect against challenge from homologous strains of influenza virus. An rHA also can be used as an immunogen in older adults. A second generation, immune refocused HA subunit vaccine as taught herein could induce protective immunity against heterologous strains as well (Treanor et al., J. Infectious Diseases 2006; 193:1223-8). Hence, for example, a candidate vaccine of interest can protect not only to the cognate antigen, such as H1, but also to different lines or isolates of HI, as well as to H2, H3, H4 and so on.

In one embodiment, the HA and NA of influenza were selected as targets for refocusing the host immune response to other non-dominant sites on HA and NA as novel targets for an immunoprotective response, preferably one of broad scope and spectrum, active on a wide variety of strains and so on.

For example, HA has five immunodominant sites or epitopes, known as A-E. Site A includes amino acids 140-146 of HA type strains and has the sequence, KRRSNKS (SEQ ID NO:1). In the Wyoming strain, that site already has three glycosylation sites associated therewith as compared to the Hong Kong strain. Thus, one approach is to remove the loop structure defined by site A, for example, by replacement of the KRRSNKS (SEQ ID NO:1) sequence by, for example, GG.

Site B includes amino acids 189-197 of HA with the sequence SDQISLYAQ (SEQ ID NO:2). That forms a helix which interacts with amino acids 158-161 having the sequence, KYKY (SEQ ID NO:3). A number of possible changes can be made to the B site, such as substitute NAS for QIS; substitute NIT for SLY; substitute NST for KYK at 158; and substitute NTS for YKY at 159, all of those changes introducing an N-glycosylation sequence at those four sites.

Site C includes amino acids 276-278 having the sequence KCN. NCT can substitute for KCN.

Site D includes a large antiparallel loop at amino acids 201-220. The entire loop can be deleted. Also, the glycosylation site, NIT, can substitute for RIT at sites 201-203.

Site E includes amino acids 79-82, FQNK (SEQ ID NO:4). The glycosylation site, NET, can substitute for QNK.

The above changes can be combined, such as, either of the NST and NTS changes at site B can be combined with the suggested, exemplary changes to sites C and/or E.

The above alterations to immunodominant sites can be obtained by cloning, site-directed mutagenesis, gene synthesis amplification and so on as taught herein and as known in the art.

Thus, the A site change above can be obtained by site-directed mutagenesis using the primers, ATop: GGAACAAGCTCTGCTTGCggcggtTTCTTTAGTAGATTGAATTGG (SEQ ID NO:5) and ABottom: CCAATTCAATCTACTAAAGAAaccgccGCAAGCAGAGCTTGTTCC (SEQ ID NO:6) to obtain the sequence, GTSSACGGFFSRLN (SEQ ID NO:7) containing the deletion described above and insertion of the GG dipeptide at that deletion site.

The B site changes can be obtained by using primers, B1Top: CAAATCAGCCTATATGCTaatGCATCAGGAAGAATCAC (SEQ ID NO:8) and B1bottom: GTGATTCTTCCTGATGCattAGCATATAGGCTGATTTG (SEQ ID NO:9) to yield the sequence QISLYANASGRI (SEQ ID NO:10); the primers B2Top: CACCACCCGGTTACGGACaatGACacAATCAGCCTATATGCTCAAGC (SEQ ID NO:11) and B2bottom GCTTGAGCATATAGGCTGATTgtGTCattGTCCGTAACCGGGTGGTG (SEQ ID NO:12) to yield the sequence HHPVTDNDTISLYAQ (SEQ ID NO:13); the primers B3Top: CGGACAGTGACCAAATCAatCTAtcTGCTCAAGCATCAGGAAG (SEQ ID NO:14) and B3Bottom: CTTCCTGATGCTTGAGCAgaTAGatTGATTTGGTCACTGTCCG (SEQ ID NO:15) to yield the sequence DSDQINLSAQASG (SEQ ID NO:16); the primers B4top: GAATTGGTTGACCCACTTAAAtTACAcATACCCAGCATTGAACGTGAC (SEQ ID NO:17) and B4bottom: GTCACGTTCAATGCTGGGTATgTGTAaTTTAAGTGGGTCAACCAATTC (SEQ ID NO:18) to yield the sequence NWLTHLNYTYPALNV (SEQ ID NO:19); and the primers B5top: GAATTGGTTGACCCACTTAAAAaACAAAacCCCAGCATTGAACGTGACTAT G (SEQ ID NO:20) and B5bottom: CATAGTCACGTTCAATGCTGGGgtTTTGTtTTTAAGTGGGTCAACCAATTC (SEQ ID NO:21) to yield the sequence NWLTHLKNKTPALNVTM (SEQ ID NO:22).

The C site change can be obtained using the primers C1top: GATCAGATGCACCCATTGGCAAtTGCAgTTCTGAATGCATCACTCC (SEQ ID NO:23) and C1bottom: GGAGTGATGCATTCAGAAcTGCAaTTGCCAATGGGTGCATCTGATC (SEQ ID NO:24) to yield the sequence SDAPIGNCSSECIT (SEQ ID NO:25).

The D site change can be obtained using the primers D1Top: CTATATGCTCAAGCATCAGGAAatATCACAGTCTCTACCAAAAG (SEQ ID NO:26) and D1Bottom: CTTTTGGTAGAGACTGTGATatTTCCTGATGCTTGAGCATATAG (SEQ ID NO:27) to obtain the sequence LYAQASGNITVSTKRS (SEQ ID NO:28).

The E site change can be obtained using the primers E1Top: GATGGCTTCCAAAATAAGAcATGGGACCTTTTTGTTGAAC (SEQ ID NO:29) and E1bottom: GTTCAACAAAAAGGTCCCATgTCTTATTTTGGAAGCCATC (SEQ ID NO:30) to yield the sequence DGFQNKTWDLFVE (SEQ ID NO:31).

The HAS1: CAGTCCTCATCAGATCCTTG (SEQ ID NO:32), HAS2: GGTAAGGGATATCTCCAGCAG (SEQ ID NO:33) primers can be used for sequencing, with HAS3: cgcgattgcgccaaatatgcc (SEQ ID NO:34) as a negative.

Many of the antigenic sites are rich in charged amino acid residues. Another approach is to replace those charged residues by substituting alanine residues therefor. Examples of such changes include KRR to AGA in site A; KYKY (SEQ ID NO:3) to AYKY (SEQ ID NO:35) and SDQI (SEQ ID NO:41) to SAQI (SEQ ID NO:36) in site B; KCN to ACN in site C and RIT to AIT in site D.

In addition, a mutation to assess the function of the hydrophobic tyrosine residue in site B can be obtained replacing SLY with SLT.

In addition to B cell epitopes, T cell epitopes also can be immunodampened. A major $CD_4$ epitope in the region of residues 177 to 199 comprises an MHC Class II binding epitope outside of the already targeted B site. Mutations in the residues LYIWGVHHP (SEQ ID NO:37) to dampen the T cell response include replacing LYIW (SEQ ID NO:42) with VYIW (SEQ ID NO:38) or VTIW (SEQ ID NO:39); and replacing VHHP (SEQ ID NO:43) with IHAG (SEQ ID NO:40).

In another embodiment, a recombinant polypeptide of interest comprising one or more immunodampened epitopes, or a vehicle comprising same, such as, a virus-like particle, a subunit composition of a virus, can be used as immunogen to obtain specific antibody or antiserum thereto that recognizes epitopes not normally but now immunogenic because of immunodampening of immunodominant epitope(s). The antibody can be made using materials and methods known in the art, and thus, can be polyclonal, by immunizing animals and collecting serum or could be obtained from humans exposed to same, similar to the current practice of administering immune globulin, or can be monoclonal practicing known materials and methods. It may be beneficial to practice methods for obtaining a humanized or human antibody, and to manipulate said antibodies to minimize immunogenicity, such as appending carbohydrate, such as PEG molecules, and other substituents to mask immunogenic sites on that influenza antibody to epitopes that are not normally immunodominant, as known in the art, see, for example, U.S. Pat. No. 5,821,337 and WO09/32661. The antibody can be collected and administered as a passive vaccine.

For testing, the immunogen of interest is administered to a nonhuman mammal for the purpose of obtaining preclinical data, for example. Exemplary nonhuman mammals include nonhuman primates, dogs, cats, rodents and other mammals. Such mammals may be established animal models for a disease to be treated with the formulation, or may be used to study toxicity of the immunogen of interest. In each of those embodiments, dose escalation studies may be performed in the mammal.

To obtain approval from regulatory agencies, such as the U.S. Food and Drug Administration or European Medicines Agency for human products, biological pharmaceutics must meet purity, safety and potency standards defined by the pertinent regulatory agency. To produce a vaccine that meets those standards, the recombinant organisms can be maintained in culture medium that is, for example, certified free of transmissible spongiform encephalopathies (herein referred to as "TSE").

Hence, for example, plasmids harboring the vaccine-encoding sequence can carry a non-antibiotic selection marker, since it is not always ideal to use antibiotic resistance markers for selection and maintenance of plasmids in bacteria that are designed for use in humans, although a preferred embodiment relates to use of a recombinant subunit vaccine. In one embodiment, therefore, the present disclosure provides a selection strategy in which, for example, a catabolic enzyme is utilized as a selection marker by enabling the growth of bacteria in medium containing a substrate of said catabolic enzyme as a carbon source. An example of such a catabolic enzyme includes, but is not restricted to, lacYZ encoding lactose uptake and β-galactosidase (GenBank Nos. J01636, J01637, K01483 or K01793). Other selection markers that provide a metabolic advantage in defined media include, but are not restricted to, galTK (GenBank No. X02306) for galactose utilization, sacPA (GenBank No. J03006) for sucrose utilization, trePAR (GenBank No. Z54245) for trehalose utilization, xylAB (GenBank No. CAB13644 and AAB41094) for xylose utilization etc. Alternatively, the selection can involve the use of antisense mRNA to inhibit a toxic allele, such as the sacB allele (GenBank No. NP_391325).

The specific method used to formulate the novel vaccines and formulations described herein is not critical to the present disclosure and can be selected from or can include a physiological buffer (Felgner et al., U.S. Pat. No. 5,589,466 (1996)); aluminum phosphate or aluminum hydroxyphosphate (e.g. Ulmer et al., Vaccine, 18:18 (2000)), monophosphoryl-lipid A (also referred to as MPL or MPLA; Schneerson et al. J. Immunol., 147:2136-2140 (1991); e.g. Sasaki et al. Inf. Immunol., 65:3520-3528 (1997); and Lodmell et al. Vaccine, 18:1059-1066 (2000)), QS-21 saponin (e.g. Sasaki et al., J. Virol., 72:4931 (1998)); dexamethasone (e.g., Malone et al., J. Biol. Chem. 269:29903 (1994)); CpG DNA sequences (Davis et al., J. Immunol., 15:870 (1998)); interferon-α (Mohanty et al., J. Chemother. 14(2):194-197, (2002)), lipopolysaccharide (LPS) antagonist (Hone et al., J. Human Virol., 1: 251-256 (1998)) and so on. Use of and commercial availability of adjuvants is a design choice, as known in the art.

Because the immune refocusing technology of interest is independent of adjuvants and immune modulators, the antigens generated practicing the methods taught herein or antibodies reactive therewith are compatible with adjuvants, such as, Alhydrogel and novel compositions developed by companies such as Novartis and GlaxoSmithKline (e.g., MF59 and AS03) and with modulators and enhancers such as CpG and cytokines.

The formulation herein also may contain more than one active compound as necessary for the particular indication being treated, preferably those with complementary activities that do not adversely impact each other. For example, it may be desirable to further provide an adjuvant. Such molecules suitably are present in combination in amounts that are effective for the purpose intended. The adjuvant can be administered sequentially, before or after antigen administration.

The immunogen of interest can be used with a second component, such as a therapeutic moiety conjugated to or mixed with same, administered as a conjugate, separately in combination, mixed prior to use and so on as a therapeutic, see, for example, Levine et al., eds., New Generation Vaccines. 2nd Marcel Dekker, Inc., New York, N.Y., 1997). The other therapeutic agent(s) can be any drug, vaccine and the like used for an intended purpose. Thus, the therapeutic agent can be a biological, a small molecule and so on. The immunogen of interest can be administered concurrently or sequentially with a second influenza immunogenic composition, a third second influenza immunogenic composition and so on, immunodampened or not, for example. Thus, an immunodampened antigen of interest can be combined with an existing vaccine to form a bivalent vaccine, a trivalent vaccine and so on, although that approach would minimize the use thereof if the existing vaccine is made in eggs. Alternatively, an immunodampened antigen of interest can be combined with more than one other antigen, subunit, component, VLP and so on to form a polyvalent vaccine.

The term "small molecule" and analogous terms include, but are not limited to, peptides, peptidomimetics, amino acids, amino acid analogues, polynucleotides, polynucleotide analogues, carbohydrates, lipids, nucleotides, nucleotide analogues, organic or inorganic compounds (i.e., including heterorganic and/organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, combinations thereof and other pharmaceutically acceptable forms of such compounds which stimulate an immune response or are immunogenic, or have a desired pharmacologic activity.

Thus, the immunogen of the disclosure may be administered alone or in combination with other types of treatments, including a second immunogen or a treatment for the disease being treated. The second component can be an immunostimulant.

In addition, the immunogen of the instant disclosure may be conjugated to various effector molecules such as heterologous polypeptides, drugs and so on, see, e.g., WO 92/08495; WO 91/14438; WO 89/12624; U.S. Pat. No. 5,314,995; and EPO 396,387. An immunogen may be conjugated to a therapeutic moiety such as an antibiotic (e.g., a therapeutic agent) or an adjuvant.

Therapeutic compounds of the disclosure alleviate at least one symptom associated with influenza. The products of the disclosure may be provided in pharmaceutically acceptable compositions as known in the art or as described herein. The terms "physiologically acceptable," "pharmacologically acceptable" and so on mean approved by a regulatory agency of the Federal or a state government or listed in the U.S. Pharmacopeia or other generally recognized pharmacopeia for use in humans.

The products of interest can be administered to a mammal in any acceptable manner. Methods of introduction include, but are not limited to, parenteral, subcutaneous, transdermal, intraperitoneal, intrapulmonary, intranasal, epidural, inhalation and oral routes, and if desired for immunosuppressive treatment, intralesional administration. Parenteral infusions include intramuscular, intradermal, intravenous, intraarterial or intraperitoneal administration. The products or compositions may be administered by any convenient route, for example, by infusion or bolus injection, by absorption through epithelial or mucocutaneous linings (e.g., oral mucosa, rectal and intestinal mucosa etc.) and may be administered together with other biologically active agents. Administration can be systemic or local. In addition, it may be desirable to introduce the therapeutic products or compositions of the disclosure into the central nervous system by any suitable route, including intraventricular and intrathecal injection; intraventricular injection may be facilitated by an intraventricular catheter, for example, attached to a reservoir, such as an Ommaya reservoir. In addition, the product can be suitably administered by pulse infusion, particularly with declining doses of the products of interest. Preferably the dosing is given by injection, preferably intravenous or subcutaneous injections, depending, in part, on whether the administration is brief or chronic.

Various other delivery systems are known and can be used to administer a product of the present disclosure, including, e.g., encapsulation in liposomes, microparticles or microcapsules (see Langer, Science 249:1527 (1990); Liposomes in the Therapy of Infectious Disease and Cancer, Lopez-Berestein et al., eds., (1989)).

The active ingredients may be entrapped in a microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, A. Osal, Ed. (1980).

Pulmonary administration can also be employed, e.g., by use of an inhaler or nebulizer, and formulation with an aerosolizing agent. The composition of interest may also be administered into the lungs of a patient in the form of a dry powder composition, see e.g., U.S. Pat. No. 6,514,496.

It may be desirable to administer the therapeutic products or compositions of the disclosure locally to the area in need of treatment; that may be achieved by, for example, and not by way of limitation, local infusion, topical application, by injection, by means of a catheter, by means of a suppository or by means of an implant, said implant being of a porous, non-porous or gelatinous material, including hydrogels or membranes, such as silastic membranes or fibers. Preferably, when administering a product of the disclosure, care is taken to use materials to which the protein does not absorb or adsorb.

In yet another embodiment, the product can be delivered in a controlled release system. In one embodiment, a pump may be used (see Langer, Science 249:1527 (1990); Sefton, CRC Crit. Ref. Biomed. Eng. 14:201 (1987); Buchwald et al., Surgery 88:507 (1980); and Saudek et al., NEJM 321: 574 (1989)). In another embodiment, polymeric materials can be used (see Medical Applications of Controlled Release, Langer et al., eds., CRC Press (1974); Controlled Drug Bioavailability, Drug Product Design and Performance, Smolen et al., eds., Wiley (1984); Ranger et al., J. Macromol. Sci. Rev. Macromol. Chem. 23:61 (1983); see also Levy et al., Science 228:190 (1985); During et al., Ann. Neurol. 25:351 (1989); and Howard et al., J. Neurosurg. 71:105 (1989)). In yet another embodiment, a controlled release system can be placed in proximity of the therapeutic target.

Sustained release preparations may be prepared for use with the products of interest. Suitable examples of sustained release preparations include semi-permeable matrices of solid hydrophobic polymers containing the immunogen, which matrices are in the form of shaped articles, e.g., films or matrices. Suitable examples of such sustained release matrices include polyesters, hydrogels (for example, poly (2-hydroxyethylmethacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers (such as injectable microspheres composed of lactic acid-glycolic acid copolymer) and poly-D-(−)-3-hydroxybutyric acid. While polymers, such as, ethylene-vinyl acetate and lactic acid-glycolic acid enable release of molecules for over 100 days, certain hydrogels release cells, proteins and products for and during shorter time periods. Rational strategies can be devised for stabilization depending on the mechanism involved.

The compositions can take the form of solutions, suspensions, emulsion, tablets, pills, capsules, powders, sustained-release formulations, depots and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate etc. Examples of suitable carriers are described in "Remington's Pharmaceutical Sciences," Martin. Such compositions will contain an effective amount of the immunogen preferably in purified form, together with a suitable amount of carrier so as to provide the form for proper administration to the patient. As known in the art, the formulation will be constructed to suit the mode of administration.

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable or are generally regarded as safe.

An immune refocused polypeptide (which includes an antigen, a portion thereof, an epitope, a determinant and so on, which can be produced as a subunit substantially free of contaminating proteins, including other influenza proteins, in combination with other viral or non-viral polypeptides; as an IR polypeptide of interest which can be expressed or produced in recombinant viruses, VLP's or in combination with one or more proteins of virus or cell origin; as an IR polypeptide which can be expressed or produced as an isolated molecule and then combined with one or more proteins of virus or cell origin; and so on, or an antibody thereto) can be obtained or made in substantially pure form. An "isolated" or "purified" immunogen or vaccine is substantially free of contaminating proteins from the medium from which the immunogen or vaccine is obtained, or substantially free of chemical precursors or other chemicals in the medium used which contains components that are chemically synthesized. The language "substantially free of subcellular material" includes preparations of a cell in which the cell is disrupted to form components which can be separated from subcellular components of the cells, including dead cells, and portions of cells, such as cell membranes, ghosts and the like, from which the immunogen or vaccine is isolated or recombinantly produced. Thus, an immunogen or vaccine that is substantially free of subcellular material includes preparations of the immunogen or vaccine having less than about 30%, 25%, 20%, 15%, 10%, 5%, 2.5% or 1%, (by dry weight) of subcellular contaminants, or any other element that differs from the product of interest.

As used herein, the terms "stability" and "stable" in the context of a liquid formulation comprising an immunogen or vaccine refer to the resistance of the immunogen or vaccine in a formulation to thermal and chemical aggregation, degradation or fragmentation under given manufacture, preparation, transportation and storage conditions, such as, for one month, for two months, for three months, for four months, for five months, for six months or more. The "stable" formulations of the disclosure retain biological activity equal to or more than 80%, 85%, 90%, 95%, 98%, 99% or 99.5% under given manufacture, preparation, transportation and storage conditions. The stability of said immunogen or vaccine preparation can be assessed by degrees of aggregation, degradation or fragmentation by methods known to those skilled in the art, including, but not limited to, physical observation, such as, with a microscope, particle size and count determination and so on, compared to a reference.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, ethanol and the like. The composition, if desired, can also contain minor amounts of wetting or emulsifying agents, or pH or buffering agents. The carrier can include a salt and/or buffer.

Buffering agents help to maintain the pH in the range which approximates physiological conditions. Buffers are preferably present at a concentration ranging from about 2 mM to about 50 mM. Suitable buffering agents for use with the instant disclosure include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid-monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present disclosure include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers may be present to ensure physiological isotonicity of liquid compositions of the instant disclosure and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably about 1% to about 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on. Stabilizers can be present in the range from 0.1 to 10,000 w/w per part of immunogen.

Additional miscellaneous excipients include bulking agents, (e.g., starch), chelating agents (e.g., EDTA), antioxidants (e.g., ascorbic acid, methionine or vitamin E) and cosolvents.

As used herein, the term "surfactant" refers to organic substances having amphipathic structures, namely, are composed of groups of opposing solubility tendencies, typically an oil-soluble hydrocarbon chain and a water-soluble ionic group. Surfactants can be classified, depending on the charge of the surface-active moiety, into anionic, cationic and nonionic surfactants. Surfactants often are used as wetting, emulsifying, solubilizing and dispersing agents for various pharmaceutical compositions and preparations of biological materials.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

As used herein, the term, "inorganic salt," refers to any compound, containing no carbon, that results from replacement of part or all of the acid hydrogen or an acid by a metal or a group acting like a metal, and often is used as a tonicity adjusting compound in pharmaceutical compositions and preparations of biological materials. The most common inorganic salts are NaCl, KCl, $NaH_2PO_4$ etc.

The present disclosure can provide liquid formulations of an immunogen or vaccine having a pH ranging from about 5.0 to about 7.0, or about 5.5 to about 6.5, or about 5.8 to about 6.2, or about 6.0, or about 6.0 to about 7.5, or about 6.5 to about 7.0.

The instant disclosure encompasses formulations, such as, liquid formulations having stability at temperatures found in a commercial refrigerator and freezer found in the office of a physician or laboratory, such as from about −20° C. to about 5° C., said stability assessed, for example, by microscopic analysis, for storage purposes, such as for about 60 days, for about 120 days, for about 180 days, for about a year, for about 2 years or more. The liquid formulations of the present disclosure also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10% (w/v).

The formulations to be used for in vivo administration must be sterile. That can be accomplished, for example, by filtration through sterile filtration membranes. For example, the subcellular formulations of the present disclosure may be sterilized by filtration.

In the case of an oral preparation, a formulation of interest can include one or more of a flavorant, odorant, scent, colorant, surfactant, binder and so on to provide a more palatable form for ingestion.

The immunogen or vaccine composition will be formulated, dosed and administered in a manner consistent with good medical practice. Factors for consideration include severity of the disease, the particular mammal being treated, the clinical condition of the individual patient, the cause of the disorder, the site of delivery of the agent, the method of administration, the scheduling of administration, and other factors known to medical practitioners. The "therapeutically effective amount" of the immunogen or vaccine thereof to be administered will be governed by such considerations, and can be the minimum amount necessary to prevent, ameliorate or treat a targeted disease, condition or disorder.

The amount of antigen or vaccine is an amount sufficient to induce the desired humoral and/or cell mediated immune response or protective in the target host. The amount of immunogen or vaccine of the present disclosure to be administered will vary depending on the species of the subject, physical characteristics of the host, such as age, weight and so on, preferred mode of delivery and so on. Generally, the dosage employed can be about 10 to about 1500 μg/dose. In comparison, the current subunit preparations contain elements from three subtypes of virus. The trivalent vaccines generally contain about 7 to about 25 μg of HA from each of the three contributing strain. That can serve as a starting point for titrating a vaccine composition of interest.

As used herein, the term "effective amount" refers to the amount of a therapy (e.g., a prophylactic or therapeutic agent), which is sufficient to reduce the severity and/or duration of a targeted disease, ameliorate one or more symptoms thereof, prevent the advancement of a targeted disease or cause regression of a targeted disease, or which is sufficient to result in the prevention of the development, recurrence, onset, or progression of a targeted disease or one or more symptoms thereof. For example, a treatment of interest can increase survivability of the host or reduce the severity of disease, based on baseline or a normal level, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another embodiment, an effective amount of a therapeutic or a prophylactic agent reduces the symptoms of a targeted disease, such as a symptom of influenza or duration of illness by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Also used herein as an equivalent is the term, "therapeutically effective amount."

Where necessary, the composition may also include a solubilizing agent and a local anesthetic such as lidocaine or other "caine" anesthetic to ease pain at the site of the injection.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration. Alternatively, the ampoule can comprise a fluid containing the active agent of interest, for example, as a concentrate for dilution prior to use or in a form ready for administration. In another embodiment, a formulation of interest is provided in a dose and volume suitable for a single, ready to use presentation.

An article of manufacture containing materials useful for the treatment of the disorder described hereinabove is provided. The article of manufacture can comprise a container and a label. Suitable containers include, for example, bottles, vials, syringes and test tubes. The containers may be formed from a variety of materials such as glass or plastic. The container holds a composition of interest and may have a sterile access port (for example, the container may be an intravenous solution bag or a vial having a stopper pierceable by a hypodermic injection needle). The label on or associated with the container indicates that the composition is used for treating influenza. The article of manufacture may further comprise a second container comprising a pharmaceutically acceptable buffer, such as phosphate-buffered saline, Ringer's solution or dextrose solution. It may further include other materials desirable from a commercial and user standpoint, including buffers, diluents, filters, needles, syringes and package inserts with instructions for use.

The instant disclosure also includes kits, e.g., comprising an immunogenic or vaccine composition of interest, homolog, derivative thereof and so on, for use, for example, as a vaccine, active or passive, and instructions for the use of same and so on. The instructions may include directions for preparing the composition, derivative and so on. The composition can be in liquid form or presented as a solid form, generally, desiccated or lyophilized. The kit can contain suitable other reagents, such as a buffer, a reconstituting solution and other necessary ingredients for the intended use. A packaged combination of reagents in predetermined amounts with instructions for use thereof, such as for a therapeutic use is contemplated. In addition, other additives may be included, such as, stabilizers, buffers and the like. The relative amounts of the various reagents may be varied to provide for concentrates of a solution of a reagent, which provides user flexibility, economy of space, economy of reagents and so on. The kit can comprise a delivery means, such as a device containing a needle, such as a syringe, which, optionally can be preloaded with the composition of interest for delivery when needed.

Citation of any of the references discussed hereinabove shall not be construed as an admission that any such reference is prior art to the present disclosure. All references cited herein are herein incorporated by reference in entirety.

The disclosure now will be exemplified by the following non-limiting examples.

EXAMPLE 1

Eight immune dampened and refocused hemagglutinin genes derived from the Wyoming strain (H3N2) were designed and engineered as described above. For example, nucleotides were substituted by site-directed mutagenesis to introduce N-linked sequons leading to complex carbohydrate modifications, and/or deletions and/or charge changes of the amino acids into the five major immunogenic and highly variable sites containing the strain-specific epitopes.

Introduction of N-linked sequons was used to maximize the size of the immune dampening by each change, particularly in the larger antigenic sites while reducing the number of wild type amino acid changes required to dampen while minimizing any impact on the conformational complexity of the glycoprotein and receptor binding domain. In some cases, as few as three amino acid changes were needed. Antigenic Site B (187-196) targets both the B cell and CD4 helper T cell IDNPEs.

To expedite the study, both DNA and protein subunit vaccines were engineered. For DNA immunization, full-length hemagglutinin genes were cloned into the pTriEx vector (Invitrogen) behind the cytomegalovirus (CMV) promoter. Transient transfection of mammalian cells with the pTriEx-HA constructs demonstrated that full-length hemagglutinin genes resembling native viral proteins were expressed as trimers and could be solublized from plasma membrane extracts.

Nine groups of outbred mice were immunized with the DNA constructs containing the eight mutated and one unmodified full length wild type HA glycoproteins. A tenth group was immunized with the empty pTriEx vector for a negative control.

In addition to the DNA expression vectors, recombinant protein was produced for immunization. The HA ectodomain contains the domains for the assembly of the trimeric glycoprotein spike and binding the host cell receptor. In addition, removal of the membrane spanning and cytoplasmic domains causes recombinant HA trimers to be released into the culture supernatant. Therefore, each of the mutated HA genes was truncated at the end of the ectodomain and cloned into a vector having the phage T7 promoter. Transfection of the ectodomain vectors into cells infected with a recombinant vaccinia virus that expressed the phage T7 RNA polymerase resulted in the production of HA trimers which were secreted into the culture media. The ectodomain trimers were purified for use as protein immunogens.

Mice were pre-bled. One group of mice was used as a negative control and the other was immunized with unmodified (wild type) antigens.

In another set of experiments, mice in the principal groups were immunized by injection of 10 micrograms of DNA (in 0.1 mL sterile water) of mutated HA glycoproteins into each quadriceps muscle. After a rest of 5 weeks, the mice were boosted with a second DNA immunization. After another 4-5 weeks, the mice were again boosted by two subcutaneous immunizations of 10 micrograms each of purified ectodomain glycoprotein. The first protein immunization was formulated in Complete Freund's Adjuvant and the second in Incomplete Freund's Adjuvant. Two weeks following the final immunization, the mice were euthanized and bled out for serum.

The sera were tested for 1) reactivity to mutant and wild type HA proteins in Western blot and ELISA formats, 2) recognition of linear epitopes by peptide ELISA, 3) protection of conformational epitopes from degradation by proteases, and 4) functional testing by hemagglutination inhibition and virus neutralization of homologous and heterologous influenza strains.

Sera from mice immunized with the panel of immune refocused HA subunit engineered antigens resulted in the generation of high titer antisera as measured by an HA-specific ELISA. All groups of mice exhibited titers to wild type HA in the range of 1:100-300,000. Down selection of the various mutated HA glycoproteins were made based on the ability of the antisera to exhibit cross subtype HI antibody in a standard HI assay.

Mutants A2, B1, B2, B3, CE, CEB4, CEB5, and D1 of H3N2 A/Wyoming/03/2003 gave equal to or higher cross subtype HI and/or virus neutralization titers against a panel of heterologous virus subtypes used in the assay. Thus, immune dampening and refocusing resulted in the production of HA glycoprotein subunit vaccine candidates capable of inducing significantly improved cross-subtype anti-viral protection as measured in vitro by standardized and accepted surrogate HI and virus neutralization assays.

Mutant A2 is the mutation in the A epitope of HA wherein KRRSNKS (SEQ ID NO:1) is replaced by GG. B1 is the mutation in the B epitope of HA wherein a glycosylation site is introduced at amino acid 197 (QIS to NAS). B2 is the mutation in the B epitope of HA wherein a glycosylation site is introduced at amino acid 189 (SDQ to NVT). B3 is the mutation in the B epitope of HA wherein a glycosylation site is introduced at amino acid 193 (SLY to NIT). CE contains two mutations, a glycosylation site is introduced into the C epitope at position 276 (KCN→NCT) and a glycosylation site is added into the E epitope at position 83 (NKK→NKT). CEB4 is CE with an additional mutation in the B epitope, a glycosylation site is added at position 158 (KYK→NST). CEB5 is the CE with an additional mutation in the B epitope, a glycosylation site was added at position 159. D1 is the mutation in the D epitope of HA wherein a glycosylation site is introduced at amino acid 201 (RIT to NIT).

In another set of experiments, refocused polypeptide antigens were tested for hemagglutinin inhibition titer and serum neutralization titer when compared to different strains of H3N2 virus. The mutants were derived from the A/Wyoming/2003 strain. M3 has the B2 epitope; M5 has the CE epitopes; and M6 has the B4CE epitopes as described above. Mice were exposed to the various muteins, A/Wyoming/2003 strain virus as the wild type positive control and carrier alone as the negative control. Mouse serum was then tested for hemagglutinin inhibition titers against three strains, the cognate Wyoming strain, Panama/1999 and Wellington/

2004 strains. Other mouse serum was tested for serum neutralization titers against the cognate Wyoming strain, Korea/2003, Korea/2002, Fujian/2002, Brisbane/09/2006 and Brisbane/10/2007 strains. Control sera from mice exposed to carrier alone generated no specific hemagglutinin inhibition antibody that reacted with the Wyoming, Panama and Wellington strains (titer=10).

Mice exposed to wild type Wyoming virus generated antiserum reactive with the Wyoming and Wellington strains (titer=1280), and marginally with the Panama strain (titer=226). The M5 mutant produced antisera that reacted twice as vigorously as wild type with the Wyoming and Wellington strains (titer=2560) and just slightly less with the Panama strain (titer=1920). The M6 mutant generated antisera that reacted at about the same level as did the M5 mutant with Panama and Wyoming strains (titers=2560 and 1280, respectively). The M6 mutant however generated a high inhibiting antiserum with a titer four times higher than all other titers, when exposed to the Wellington strain (titer=10240).

Thus, immunorefocusing resulted in broadened responses against two other strains aside from the cognate strain, along with a very high response against the Wellington strain when the triple modified mutein was used. In the neutralization studies, mice exposed to carrier produced no specific antibody. Mice exposed to Wyoming generated antisera that reacted strongly with Wyoming (titer=640); the titer for Korea and Brisbane 2006 was a quarter that of Wyoming (titer=160); and there was essentially no reactivity with Brisbane 2007 (titer=20). The M3 mutein generated in mice antisera that was four time as reactive as wild type immunogen on Wyoming, Brisbane 2006 and Brisbane 2007 (titer=2560). That antisera did not react with Korea (titer=3). Mice exposed to M5 generated antisera reactive with Wyoming (titer=80), was twice as reactive with Brisbane 2006 (titer=160) and thirty times as reactive with Korea (titer=2560). That antisera was substantially unreactive with Brisbane 2007 (titer=20). Thus, broadened responses to three other strains were obtained with the immune refocused antigens of interest.

Thus, a composition of interest stimulated protective immunity against viruses that exist in the future relative to the parental strain, as well as against viruses that were more commonly found in the past. Thus, an immune refocused H3N2 vaccine based on Brisbane/07 will stimulate protective responses against viruses not yet evolved and, thereby, avoid the necessity of reformulating over the next several years. An immune refocused Wyoming-based or Brisbane-based vaccine can be developed to protect against all H3N2 strains, both past and future.

EXAMPLE 2

The design of immune refocused hemagglutinin antigens of the swine-like H1N1v A/California/04/2009 strain is based on multiple considerations, including analyses of immunodominant epitopes, evolution and sequence diversity and structural data. The following mutations are designed to refocus immune responses away from immunodominant, highly variable sites and toward more broadly protective epitopes.

As taught herein, immune refocusing mutations can take several forms including deletions, addition or subtraction of glycosylation sites as well as substitutions that affect charge, hydropathy, or some other chemical property of an epitope. Glycosylation additions have the advantage of masking epitopes with a relatively large moiety while charge changes focus on particular sites where antibody interacts with antigen. Because of the high degree of structural similarity among HA proteins of various influenza strains and serotypes, analysis of 3-D structures of the related A/PR8/34 was used to identify putative loops and other flexible sites of the HA sequence. The HA of A/California/04/2009 was aligned with A/PR8/34 HA to transpose the identified residues of PR8 to Cal/04/09.

FIG. 2 provides Table 2 which presents single-site mutations intended to refocus immunity toward more broadly protective responses. The initial proposed mutations are comprised largely of amino acid substitutions that affect glycosylation patterns and/or local charge elements. The mutations were selected based on available sequence and structural data used to identify immunodominant epitopes that contribute to strain-specific responses.

The sequences and mutations are arranged in Table 2 to correlate to epitope sites along the HA glycoprotein starting at the N-terminus. Residues comprising the C-terminal portion of the D site (starting at 214) and the fusion domain (starting at 314) have been offset to conserve space in the table.

The mutations were designed as follows:

(i) Mutations M1 and M3 of Epitope C and M6 and M7 of Epitope E were selected as being in or closely near sites implicated as binding monoclonal antibodies. Because they are in highly flexible loops and in regions of high sequence variability, we predict that they contribute to strain-specific immunity;

(ii) Mutations M1, M2, M5, M6, M8, M9, M10, M14, M16, M18, M20, M22, M23, and M25 serve the dual purposes of introducing a glycosylation site into an immunodominant, strain-specific site while simultaneously altering the charges associated with amino acids in the epitopes;

(iii) Mutations M3, M4, M7, M11, M12, M13, M15, M17, M19, M21, M24, and M26 substitute charged amino acid residues with uncharged residues;

(iv) Mutation M5 serves the specific purpose of adding a glycosylation to the E epitope to refocusing immunity towards conserved elements in the fusion domain or the HA-1 HA-2 fusion site (as do other C and E mutations); and (v) Mutations M25 and M26 target an immunodominant site located close to the HA1-HA2 cleavage site and fusion domain (denoted site 'f' in Table 1) to refocus immunity to these highly conserved loci.

FIG. 3 identifies a subset of the single-site mutations superimposed on the structure of the A/PR8/34 HA structure. FIG. 1 demonstrates that the mutations have largely been inserted into highly flexible loops to mask epitopes without disrupting the native-like folding of the recombinant proteins. Insertion of mutations into the variable loops ensures that most conformational epitope can be formed

EXAMPLE 3

HA mutations can be engineered using, for example, known methods such as, site-specific mutagenesis (quick-change) or, for example, gene synthesis. In general, a quick-change mutation can be used for derivation of single or double mutations while gene synthesis can be used for more complex combinations.

Single-site mutations are most helpful in assessing immune refocusing techniques directed to specific residues of each epitope. However, because pathogens utilize more than one immunodominant, variable epitope (deceptive epitope or decotope) to evade long-term immune pressure, improved immune refocused antigens can incorporate mutations to multiple antigenic sites. Examples of immune refocused HA antigens containing mutations in 2 or 3 epitopes are provided in FIG. 4 which presents Table 3. Examples of immune refocused HA antigens containing mutations in all five epitopes are provided in FIG. 5 which presents Table 4. In both Tables 3 and 4, the mutations are comprised of combinations of the single-site mutations presented in FIG. 2 which presents Table 2. Analysis of structural models, as shown in FIG. 3, is useful in the design of combination mutations so that the mutations selected will have reduced probability of interfering with each other in terms of charge, steric inhibition, or other negative consequence.

For the purposes of evaluation of immune refocused HA candidates, it is instructive to test combinations of mutations in which some combinations are composed of glycosylation insertions while other combinations are largely composed of substitutions that only reduce electrostatic charge in the epitopes.

The lists of mutations in the Tables are for the purposes of example in training in the art and that once trained, additional mutations designed in similar sites or for similar purposes can be obtained practicing the materials and methods taught herein.

Antigens based on the H1N1 HA sequences that are described in Example 3 may be used as a vaccine to stimulate broadened immunity against all H1N1 variants. Additional mutations can be made as taught herein such that the H1N1-based antigen can stimulate protective immunity against influenza strains from other serotypes, such as, H2, H5 and so forth.

The antigen design method taught herein can be used to produce vaccines or antibodies based on other serotypes of influenza, such as, H2N2, H5N1, H7, H9 and others.

Such mutations can be designed to stimulate immunity for the purpose of producing a broadly reactive antibody that can be used for therapeutics, diagnostics or other applications.

The combined use of adjuvants with such mutations can lead to additional improvements in the breadth of cross-reactive immunity.

EXAMPLE 4

The safety, toxicity and potency of recombinant immunogens are evaluated according to the guidelines in 21 CFR 610, which include: (i) general safety tests, as well as acute and chronic toxicity tests.

Immunogenicity data are derived from an accepted animal model that responds well to human influenza vaccine (e.g. guinea pigs, mice, ferrets or cotton rats). The investigations include an evaluation of immune responses according to dose and dose intervals using vaccine that contains the strain intended for the final product. Immunogenicity studies in relevant animal models are used to document consistency of production, in particular during the validation phase of a vaccine for novel influenza viruses manufacturing process. Suitable non-clinical endpoints selected for the animal studies include death, weight loss, virus excretion rates, clinical signs such as fever, oculo-nasal secretions and so on.

Groups of ferrets or other suitable animals are inoculated intraperitoneally with 100 μl of immunogen containing 300 μg of the immunogen of interest. Suitable negative and positive controls are used.

The animals are monitored for general health and body weight for 14 days post infection. Similar to animals that receive placebo, animals that receive the immunogen remain healthy, and do not lose weight or display overt signs of disease during the observation period.

For the more stringent safety test, groups of animals are injected with 300 μg of the immunogen.

One day after inoculation, 3 animals in each group are euthanized and the spleen, lung and liver homogenates are analyzed for immunogen. At week 4, 8, 12, and 16 post-infection, 3 animals in each group are euthanized and spleen, liver and lung homogenates are obtained and analyzed to assess presence of the immunogen.

The immunogen is deemed safe if no adverse health effects are observed and the animals gain weight at the normal rate compared to animals inoculated with placebo as an internal control.

To evaluate the acute and chronic toxicity of an immunogen, groups of ferrets are inoculated intradermally with 300 μg of the immunogen at graded doses or saline.

Three days post-inoculation, 8 animals in each group are euthanized to access the acute effects of the immunogen on the animals. At 28 days post-inoculation, the remaining 8 animals in each group are euthanized to evaluate any chronic effects on the animals. At both time points, the body weight of each animal is obtained. In addition, the gross pathology and appearance of the injection sites are examined. Blood is taken for blood chemistry, and the histopathology of the internal organs and injection sites are performed at each time point.

Other animals are given a total of 3 doses of vaccine at 0, 14 and 60 days and the immune response to hemagglutinin is measured by ELISA using sera collected from the animals at 10 day intervals. The neutralization of influenza virus is measured in the collected sera, for example, 80 days after the first vaccination.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be embraced by the appended claims.

All references cited herein are herein incorporated by reference in entirety.

REFERENCES

Thomas Francis, Jr. in Proceedings of the American Philosophical Society, Vol. 104, No. 6 (Dec. 15, 1960), pp. 572-578, according to The Swine Flu Episode and the Fog of Epidemics by Richard Krause in DCD's Emerging Infectious Diseases Journal, Vol. 12, No. 1, January 2006, published Dec. 20, 2005.

Gamblin S J, Haire L F, Russell R J, Stevens D J, Xiao B, Ha Y, Vasisht N, Steinhauer D A, Daniels R S, Elliot A, Wiley D C & Skehel J J, 2004. The structure and receptor binding properties of the 1918 influenza hemagglutinin Science 303, p. 1838-1842.

Garrity, R. R., G. Rimmelzwaan, A. Minassian, W. P. Tsai, G. Lin, J. J. de Jong, J. Goudsmit & P. L. Nara. 1997. Refocusing neutralizing antibody response by targeted dampening of an immunodominant epitope. J. Immunol. 159:279-89.

Kohler H, Goudsmit, J. & Nara P. Clonal dominance: cause for a limited and failing immune response to HIV-1 infection and vaccination. J. Acquir. Immune Defic. Syndr. 1992. 5(11):1158-68.

Andreansky, S. S., John Stambas, Paul G. Thomas, Weidong Xie, Richard J. Webby, & Peter C. Doherty. Consequences of immunodominant epitope deletion for minor influenza virus-specific CD8+ T cell responses. J. Virol. 2005 April, 79(7):4329-39.

Nara, P. L. & R. Garrity. 1998. Deceptive imprinting: a cosmopolitan strategy for complicating vaccination. Vaccine 16:1780-7.

Nara, P. L., R. R. Garrity & J. Goudsmit. 1991. Neutralization of HIV-1: a paradox of humoral proportions. FASEB J. 5:2437-55.

Nara, P. L. & G. Lin. 2005. HIV-1: the confounding variables of virus neutralization. Curr. Drug Targets Infect. Disord. 5:157-70.

Trujiollo, J. D., N. M. Kumpula-McWhirter, K. J. Hotzel, M. Gonzalez & W. P. Cheevers. 2004. Glycosylation of immunodominant linear epitopes in the carboxy-terminal region of the caprine arthritis-encephalitis virus surface envelope enhances vaccine-induced type-specific and cross-reactive neutralizing antibody responses. J. Virol. 78:9190-202.

The disclosure is claimed as follows:

1. A polypeptide or virus comprising an epitope of a human influenza virus comprising an amino acid sequence selected from SEQ ID NO:45-48, 50-52, 54-59, 61-66, 71, 74-76 or 77.

2. A recombinant virus comprising the polypeptide of claim 1.

3. The recombinant virus of claim 2 comprising a therapeutic molecule.

4. The recombinant virus of claim 2, comprising an influenza virus.

5. A pharmaceutical composition comprising the polypeptide or virus of claim 1.

6. An immunogenic composition comprising the virus or polypeptide of claim 1.

7. The immunogenic composition of claim 6, further comprising an adjuvant.

8. A virus-like particle (VLP) comprising the polypeptide of claim 1.

9. The immunogenic composition of claim 7, wherein said adjuvant is an aluminum salt or a lipopolysaccharide.

10. The immunogenic composition of claim 6, further comprising a pharmaceutically acceptable carrier, diluent or excipient.

11. The virus of claim 4, wherein said influenza virus is human influenza, avian influenza, swine influenza, canine influenza or horse influenza.

12. A fusion protein comprising the polypeptide of claim 1.

13. The VLP of claim 8, further comprising a therapeutic molecule.

* * * * *

SEQUENCE LISTING

```
<160> NUMBER OF SEQ ID NOS: 77

<210> SEQ ID NO 1
<211> LENGTH: 7
<212> TYPE: PRT
<213> ORGANISM: Influenza A virus

<400> SEQUENCE: 1

Lys Arg Arg Ser Asn Lys Ser
1               5


<210> SEQ ID NO 2
<211> LENGTH: 9
<212> TYPE: PRT
<213> ORGANISM: Influenza A virus

<400> SEQUENCE: 2

Ser Asp Gln Ile Ser Leu Tyr Ala Gln
1               5


<210> SEQ ID NO 3
<211> LENGTH: 4
<212> TYPE: PRT
<213> ORGANISM: Influenza A virus

<400> SEQUENCE: 3

Lys Tyr Lys Tyr
1


<210> SEQ ID NO 4
<211> LENGTH: 4
<212> TYPE: PRT
<213> ORGANISM: Influenza A virus

<400> SEQUENCE: 4

Phe Gln Asn Lys
1


<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

ggaacaagct ctgcttgcgg cggtttcttt agtagattga attgg                    45


<210> SEQ ID NO 6
<211> LENGTH: 45
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 6
ccaattcaat ctactaaaga aaccgccgca agcagagctt gttcc 45

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Gly Thr Ser Ser Ala Cys Gly Gly Phe Phe Ser Arg Leu Asn
1 5 10

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
caaatcagcc tatatgctaa tgcatcagga agaatcac 38

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
gtgattcttc ctgatgcatt agcatatagg ctgatttg 38

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Gln Ile Ser Leu Tyr Ala Asn Ala Ser Gly Arg Ile
1 5 10

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
caccacccgg ttacggacaa tgacacaatc agcctatatg ctcaagc 47

```
<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

gcttgagcat ataggctgat tgtgtcattg tccgtaaccg ggtggtg                 47


<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His His Pro Val Thr Asp Asn Asp Thr Ile Ser Leu Tyr Ala Gln
1               5                   10                  15


<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

cggacagtga ccaaatcaat ctatctgctc aagcatcagg aag                     43


<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

cttcctgatg cttgagcaga tagattgatt tggtcactgt ccg                     43


<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Ser Asp Gln Ile Asn Leu Ser Ala Gln Ala Ser Gly
1               5                   10


<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

gaattggttg acccacttaa attacacata cccagcattg aacgtgac                48
```

-continued

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
gtcacgttca atgctgggta tgtgtaattt aagtgggtca accaattc 48

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Asn Trp Leu Thr His Leu Asn Tyr Thr Tyr Pro Ala Leu Asn Val
1 5 10 15

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
gaattggttg acccacttaa aaaacaaaac cccagcattg aacgtgacta tg 52

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
catagtcacg ttcaatgctg gggttttgtt ttttaagtgg gtcaaccaat tc 52

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Asn Trp Leu Thr His Leu Lys Asn Lys Thr Pro Ala Leu Asn Val Thr
1 5 10 15

Met

<210> SEQ ID NO 23
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
gatcagatgc acccattggc aattgcagtt ctgaatgcat cactcc 46

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ggagtgatgc attcagaact gcaattgcca atgggtgcat ctgatc 46

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Ser Asp Ala Pro Ile Gly Asn Cys Ser Ser Glu Cys Ile Thr
1 5 10

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ctatatgctc aagcatcagg aaatatcaca gtctctacca aaag 44

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
cttttggtag agactgtgat atttcctgat gcttgagcat atag 44

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Leu Tyr Ala Gln Ala Ser Gly Asn Ile Thr Val Ser Thr Lys Arg Ser
1 5 10 15

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gatggcttcc aaaataagac atgggacctt tttgttgaac 40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gttcaacaaa aaggtcccat gtcttatttt ggaagccatc 40

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Asp Gly Phe Gln Asn Lys Thr Trp Asp Leu Phe Val Glu
1 5 10

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cagtcctcat cagatccttg 20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
ggtaagggat atctccagca g 21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cgcgattgcg ccaaatatgc c 21

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Ala Tyr Lys Tyr
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ser Ala Gln Ile
1

<210> SEQ ID NO 37
<211> LENGTH: 9
<212> TYPE: PRT
<213> ORGANISM: Influenza A virus

<400> SEQUENCE: 37

Leu Tyr Ile Trp Gly Val His His Pro
1 5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Val Tyr Ile Trp
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Val Thr Ile Trp
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Ile His Ala Gly
1

<210> SEQ ID NO 41
<211> LENGTH: 4
<212> TYPE: PRT
<213> ORGANISM: Influenza A virus

<400> SEQUENCE: 41

Ser Asp Gln Ile
1

<210> SEQ ID NO 42
<211> LENGTH: 4
<212> TYPE: PRT
<213> ORGANISM: Influenza A virus

<400> SEQUENCE: 42

Leu Tyr Ile Trp
1

<210> SEQ ID NO 43
<211> LENGTH: 4
<212> TYPE: PRT
<213> ORGANISM: Influenza A virus

<400> SEQUENCE: 43

Val His His Pro
1

<210> SEQ ID NO 44
<211> LENGTH: 19
<212> TYPE: PRT
<213> ORGANISM: Influenza A virus

<400> SEQUENCE: 44

```
Leu Glu Asp Lys His Asn Gly Lys Leu Cys Lys Leu Arg Gly Val Ala
1               5                   10                  15

Pro Leu His
```

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

```
Leu Asn Ser Thr His Asn Gly Lys Leu Cys Lys Leu Arg Gly Val Ala
1               5                   10                  15

Pro Leu His
```

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

```
Leu Glu Asp Lys His Asn Gly Lys Asn Val Thr Leu Arg Gly Val Ala
1               5                   10                  15

Pro Leu His
```

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Leu Gln Asn Ile His Asn Gly Lys Leu Cys Lys Leu Arg Gly Val Ala
1 5 10 15

Pro Leu His

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Leu Glu Asp Lys His Asn Gly Lys Leu Cys Ile Leu Leu Gly Val Ala
1 5 10 15

Pro Leu His

<210> SEQ ID NO 49
<211> LENGTH: 14
<212> TYPE: PRT
<213> ORGANISM: Influenza A virus

<400> SEQUENCE: 49

Asn Pro Glu Cys Glu Ser Leu Ser Thr Ala Ser Ser Trp Ser
1 5 10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Asn Pro Glu Cys Glu Ser Leu Ser Thr Asn Ile Thr Trp Ser
1 5 10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Asn Ser Thr Cys Glu Ser Leu Ser Thr Ala Ser Ser Trp Ser
1 5 10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Asn Pro Gln Cys Gln Ser Leu Ser Thr Ala Ser Ser Trp Ser
1 5 10

<210> SEQ ID NO 53
<211> LENGTH: 26
<212> TYPE: PRT
<213> ORGANISM: Influenza A virus

<400> SEQUENCE: 53

Pro Lys Thr Ser Ser Trp Pro Asn His Asp Ser Asn Lys Gly Val Thr
1               5                   10                  15

Ala Ala Cys Pro His Ala Gly Ala Lys Ser
            20                  25

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Asn Ala Ser Ser Trp Pro Asn His Asp Ser Asn Lys Gly Val Thr
1               5                   10                  15

Ala Ala Cys Pro His Ala Gly Ala Lys Ser
            20                  25

<210> SEQ ID NO 55
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Lys Thr Ser Ser Trp Pro Asn His Asn Ile Thr Lys Gly Val Thr
1               5                   10                  15

Ala Ala Cys Pro His Ala Gly Ala Lys Ser
            20                  25

<210> SEQ ID NO 56
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Lys Thr Ser Ser Trp Pro Asn His Asp Ser Asn Lys Gly Val Thr
1               5                   10                  15

Ala Ala Cys Pro His Asn Ala Thr Gln Ser
            20                  25

<210> SEQ ID NO 57
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Ile Thr Ser Ser Trp Pro Asn His Asp Ser Asn Lys Gly Val Thr
1 5 10 15

Ala Ala Cys Pro His Ala Gly Ala Lys Ser
20 25

<210> SEQ ID NO 58
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Pro Lys Thr Ser Ser Trp Pro Asn His Asn Ser Asn Ile Gly Val Thr
1 5 10 15

Ala Ala Cys Pro His Ala Gly Ala Lys Ser
20 25

<210> SEQ ID NO 59
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Pro Lys Thr Ser Ser Trp Pro Asn His Asp Ser Asn Lys Gly Val Thr
1 5 10 15

Ala Ala Cys Pro Asn Ala Gly Ala Leu Ser
20 25

<210> SEQ ID NO 60
<211> LENGTH: 21
<212> TYPE: PRT
<213> ORGANISM: Influenza A virus

<400> SEQUENCE: 60

Lys Lys Gly Asn Ser Tyr Pro Lys Leu Ser Lys Ser Tyr Ile Asn Asp
1 5 10 15

Lys Gly Lys Glu Val
20

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Lys Asn Ala Thr Ser Tyr Pro Lys Leu Ser Lys Ser Tyr Ile Asn Asp
1 5 10 15

Lys Gly Lys Glu Val
20

<210> SEQ ID NO 62
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 62

Ile Leu Gly Asn Ser Tyr Pro Lys Leu Ser Lys Ser Tyr Ile Asn Asp
1               5                   10                  15

Lys Gly Lys Glu Val
            20


<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Asn Ala Thr Ser Thr Pro Lys Leu Ser Lys Ser Tyr Ile Asn Asp
1               5                   10                  15

Lys Gly Lys Glu Val
            20


<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Ile Gly Asn Ser Tyr Asn Lys Leu Ser Lys Ser Tyr Ile Asn Asp
1               5                   10                  15

Lys Gly Lys Glu Val
            20


<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Lys Gly Asn Ser Tyr Pro Lys Leu Ser Lys Ser Tyr Ile Asn Val
1               5                   10                  15

Asn Gly Thr Gln Val
            20


<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Lys Gly Asn Ser Tyr Pro Lys Leu Ser Lys Ser Tyr Ile Asn Asp
1               5                   10                  15

Leu Gly Ile Gln Val
            20
```

<210> SEQ ID NO 67
<211> LENGTH: 6
<212> TYPE: PRT
<213> ORGANISM: Influenza A virus

<400> SEQUENCE: 67

Gln Asn Ala Asp Thr Tyr
1               5

<210> SEQ ID NO 68
<211> LENGTH: 10
<212> TYPE: PRT
<213> ORGANISM: Influenza A virus

<400> SEQUENCE: 68

Ile Ala Ile Arg Pro Lys Val Arg Asp Gln
1               5                   10

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Asn Ala Ser Thr Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Ala Ala Asp Thr Tyr
1               5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Ala Ile Arg Pro Asn Val Thr Asp Gln
1               5                   10

<210> SEQ ID NO 72
<211> LENGTH: 11
<212> TYPE: PRT
<213> ORGANISM: Influenza A virus

<400> SEQUENCE: 72

Leu Val Glu Pro Gly Asp Lys Ile Thr Phe Glu
1               5                   10

<210> SEQ ID NO 73
<211> LENGTH: 10
<212> TYPE: PRT
<213> ORGANISM: Influenza A virus -continued

```
<400> SEQUENCE: 73

Leu Ala Thr Gly Leu Arg Asn Ile Pro Ser
1               5                   10


<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Val Glu Pro Asn Ala Thr Ile Thr Phe Glu
1               5                   10


<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Val Glu Pro Gly Asn Leu Ile Thr Phe Glu
1               5                   10


<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Ala Thr Gly Leu Asn Ile Thr Pro Ser
1               5                   10


<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Ala Thr Gly Leu Ile Asn Ile Pro Ser
1               5                   10
```